(12) United States Patent
Thompson et al.

(10) Patent No.: US 9,078,956 B2
(45) Date of Patent: Jul. 14, 2015

(54) MODIFICATION OF BIOMEDICAL POLYMERS FOR PREVENTION OF FOULING AND CLOTTING

(71) Applicant: Econous Systems Inc., Toronto (CA)

(72) Inventors: Michael Thompson, Toronto (CA); Sonia Sheikh, Willowdale (CA); Jack Chih-Chieh Sheng, Ajax (CA); Christophe Blaszykowski, Toronto (CA); Kiril Fedorov, Richmond Hill (CA)

(73) Assignee: Econous Systems Inc., Toronto, Ontario (CA)

( * ) Notice: Subject to any disclaimer, the term of this patent is extended or adjusted under 35 U.S.C. 154(b) by 14 days.

(21) Appl. No.: 13/935,526

(22) Filed: Jul. 4, 2013

(65) Prior Publication Data

US 2014/0018463 A1 Jan. 16, 2014

Related U.S. Application Data

(63) Continuation-in-part of application No. 13/154,067, filed on Jun. 6, 2011, now Pat. No. 8,491,958.

(60) Provisional application No. 61/353,383, filed on Jun. 10, 2010.

(51) Int. Cl.
```
A61L 33/00      (2006.01)
G01N 29/02      (2006.01)
G01N 29/036     (2006.01)
```

(52) U.S. Cl.
CPC .......... *A61L 33/0082* (2013.01); *G01N 29/022* (2013.01); *G01N 29/036* (2013.01); *C07B 2200/11* (2013.01); *G01N 2291/0255* (2013.01); *G01N 2291/0256* (2013.01); *G01N 2291/0426* (2013.01)

(58) Field of Classification Search
CPC .................. A61L 33/0082; C07B 2200/11
See application file for complete search history.

(56) References Cited

U.S. PATENT DOCUMENTS

| | | | |
|---|---|---|---|
| 3,843,390 A * | 10/1974 | Hudson et al. | 428/412 |
| 7,207,222 B2 | 4/2007 | Thompson et al. | |
| 7,500,379 B2 | 3/2009 | Hines | |
| 2011/0136262 A1 | 6/2011 | Ragavan et al. | |

OTHER PUBLICATIONS

Collings et al., "Biosensors: Recent Advances", Rep. Prog. Phys.b May 1, 1997, pp. 1397-1445.
Sadik et al., "Environmental Biosensors for Organochlorines, Cyanobacterial Toxins and Endocrine Disrupting Chemicals", Biotechnol. Bioprocess Eng. 2000, pp. 407-412.
Yu et al., "Biosensors in Drug Discovery and Drug Analysis", Analytical Letters, 38, Accepted Jun. 1, 2005, pp. 1687-1701.
Gooding, "Biosensor Technology For Detecting Biological Warfare Agents: Recent Progress And Future Trends", Analytica Chimica Acta 559, Available online Jan. 24, 2006, pp. 137-151.
Rusmini et al., "Protein Immobilization Strategies for Protein Biochips", Biomacromolecules 2007, 8, Published on Web Apr. 20, 2007, pp. 1775-1789.
Kim et al, "Molecular Recognition and Specific Interactions for Biosensing Applications", Sensors, Oct. 23, 2008, pp. 6605-6641.
Vericat et al., Surface Characterization of Sulfur and Alkanethiol Self-Assembled Monolayers on Au(111), Journal of Physics Condensed Matter 18, Nov. 17, 2006, pp. R867-R900.
Shenhar et al., "Self-Assembly and Self-Organization", Introduction to Nanoscale and Technology, 2004, pp. 41-74.
Ulman, "Formation and Structure of Self-Assembled Monolayers", Chem. Rev. 1996, pp. 1533-1554.
Lee et al., "Electrophilic Siloxane-Based Self-Assembled Monolayers for Thiol-Mediated Anchoring of Peptides and Proteins", Langmuir, American Chemical Society, 1993, pp. 3009-3014.
Azioune et al., "TOF-SIMS Surface and Interface Characterization of the Immobilized Camel Antibody (cAb) onto SAMs-COOH/Au Substrates", Elsevier, Applied Surface Science, Available online Apr. 27, 2004, pp. 402-405.
Chrisey et al., "Covalent Attachment of Synthetic DNA to Self-Assembled Monolayer Films", Nucleic Acids Research, Oxford University Press, vol. 24, 1996, pp. 3031-3039.
Saoud et al., "Linker Immobilization of Protein and Oligonucleotide on Indium—Tin—Oxide for Detection of Probe-Target Interactions by Kelvin Physics", Analyst, 134, Mar. 14, 2009, pp. 835-837.
Wink et al., "Self-Assembled Monolayers for Biosensors", Analyst, vol. 122, Apr. 1997, pp. 43R-50R.
Chaki et al., "Self-Assembled Monolayers as a Tunalbe Platform for Biosensor Applications", Biosensors Bioelectronics, 2001, pp. 1-12.
Luderer et al., "Immobilization of Oligonucleotides for Biochemical Sensing By Self-Assembled Monolayers: Thio-Organic Bonding on Gold and Silanization on Silica Surfaces", Top. Curr. Chem., 260, Sep. 16, 2005, pp. 37-56.

(Continued)

*Primary Examiner* — Yong Chu
(74) *Attorney, Agent, or Firm* — Kathleen Marsman; Borden Ladner Gervais LLP

(57) ABSTRACT

A surface-modified polymer is described, comprising a polymeric material and a self-assembling monolayer covalently bound thereto. The monolayer comprises monoethylene glycolated-OH (MEG-OH); 2-(3-trichlorosilyl-propyloxy)-ethyl-trifluoroacetate (7-OEG or MEG-TFA); 2,2,2-trifluoroethyl-13-trichlorosilyl-tridecanoate (TTTA); OEGylated TTTA (OEG-TTTA); S-(2-(2-(2-(3-trichlorosilyl-propyloxy)-ethoxy)-ethoxy)-ethyl)-benzenethiosulfonate (OEG-TUBTS); or a combination thereof. Methods are described for forming a surface-modified polymer by surface activation, such as with plasma. By utilizing the surface-modified polymer to make medical equipment or devices for contacting biological fluids, a reduction in surface fouling and thrombus formation can result. Advantageously, polymeric equipment or components so modified may have a reduction in unwanted chemical interactions leading to fouling or clotting. Short trichlorosilane surface modifiers allow films to be deposited onto poly(ethylene terephthalate), polycarbonate, polypropylene, polyvinyl chloride, polyurethane, and other polymers activated using plasma.

21 Claims, 19 Drawing Sheets

(56) References Cited

OTHER PUBLICATIONS

Ferretti et al., "Self-Assembled Monolayers: A Versatile Tool for the Formulation of Bio-Surfaces", Trends in Analytical Chemistry, vol. 19, No. 9, 2000, pp. 530-540.
Guilbault et al., "Analytical Uses of Piezoelectric Crystals: A Review", C R C Critical Reviews in Analytical Chemistry, vol. 19, Issue 1, Feb. 18, 1988, pp. 1-28.
Deakin et al., "Electrochemical Applications of the Quartz Crystal Microbalance", Analytical Chemistry, vol. 61, No. 20, Oct. 15, 1989, pp. 1147A-1154A.
Sheikh et al., "Acoustic Wave-Based Detection in Bionalytical Chemistry: Competition for Surface Plasmon Resonance?",Analytical Letters, 41, Available online Nov. 6, 2008, pp. 2525-2538.
Gronewold, "Surface acoustic wave sensors in the Bioanalytical field: Recent Trends and Challenges" Analytica Chimica Acta 603, 2007, pp. 119-128.
Rickert et al., "Biosensors Based on Acoustic Wave Devices", In Sensors Update, vol. 5, 1999, pp. 105-139.
Cavic et al., "Acoustic Waves and the Study of Biochemical Macromolecules and Cells at the Sensor-Liquid Interface", The Analyst, 24, Jul. 12, 1999, pp. 1405-1420.
Cooper et al., "A Survey of the 2001 to 2005 Quartz Crystal Microbalance Biosensor Literature: Applications of Acoustic Physics to the Analysis of Biomolecular Interactions", Journal of Molecular Recognition, 20, 2007, pp. 154184.
Lange et al., "Surface Acoustic Wave Biosensors: A review", Anal Bional Chem, 391, Feb. 12, 2008, pp. 1509-1519.
Ballantyne et al., "Electromagnetic Excitation of High Frequency Acoustic Waves and Detection in the Liquid Phase", The Analyst, 2003, Jul. 7, 2003, pp. 1048-1055.
Thompson et al., "Superior Analytical Sensitivity of Electromagnetic Excitation Compared to Contact Electrode Instigation of Transverse acoustic", The Analyst, Feb. 2, 2004, pp. 219-224.
McGovern et al., "Self-Assembled Silanes and the Thiol Functionalization of Surfaces", Anal. Communication, 35, Oct. 27, 1998, pp. 391-393.
McGovern et al., "Thiol Functionalization of Surfaces for Biosensor Development", Can. J. Chem., vol. 77, 1999, pp. 1678-1689.
Wasserman et al., "Structure and Reactivity of Alkylsiloxane Monolayers Formed by Reaction of Alkyltrichlorosilanes on Silicon Substrates", Langmuir, vol. 5, No. 4, 1989, pp. 1074-1087.
Fryxell et al., "Nucleophilic Displacements in Mixed Self-Assembled Monolayers", Langmuir, vol. 12, No. 21, 1996, pp. 5064-5075.
Lee et al., "Characterization of a Self-Assembled Monolayer of Thiol on a Gold Surface and the Fabrication of a Biosensor Chip Based on Surface Plasmon Resonance for Detecting Anti-GAD Antibody", Biosensors and Bioelectronics 20, Available online Jun. 19, 2004, pp. 1422-1427.
Zheng et al., "Strong Repulsive Forces Between Protein and Oligo (Ethylene Glycol) Self-Assembled Monolayers: A Molecular Simulation Study", Biophysical Journal, vol. 89, Jul. 2005, pp. 158-166.
Ostuni et al., "A Survey of Structure—Property Relationships of Surfaces that Resist the Adsorption of Protein", Langmuir, vol. 17, No. 18, 2001, pp. 5605-5620.
Ngadi et al., "Are PEG Molecules a Universal Protein Repellent?", World Academy of Science, Engineering and Technology 49, 2009, pp. 144-148.
Snellings et al., "Protein Adhesion at Poly(ethylene glycol) Modified Surfaces", Advanced Materials, vol. 12, No. 24, Dec. 15, 2000, pp. 1959-1962.
Ostuni et al., "Self-Assembled Monolayers That Resist the Adsorption of Proteins and the Adhesion of Bacterial and Mammalian Cells", Langmuir, vol. 17, No. 20, 2001, pp. 6336-6343.
Xia et al., "Functionalized Poly(ethylene glycol)-Grafted Polysiloxane Monolayers for Control of Protein Binding", Langmuir, vol. 18, No. 8, 2002, pp. 3255-3262.

Jeon et al., "Protein-Surface Interactions in the Presence of Polyethylene Oxide", Journal of Colloid and Interface Science, vol. 142, No. 1, Mar. 1, 1991, pp. 149-158.
Parsons et al., "Organic Disulfides and Related Substances. XIV. Aspects of the Reaction of Thiolsulfonates with Thiols", Journal Org. Chem. Soc., Jan. 25, 1965, pp. 1923-1926.
Kice et al., "A Kinetic Study of the Reaction of Mercaptans with Phenyl Benzenethiolsulfinate and Benzenethiolsulfonate in Aqueous Dioxane", Journal of the American Chemical Society, May 30, 1974, pp. 8015-8019.
Delgado et al., "Ring-Closing Metathesis in the Synthesis of Large and Medium-Sized Oxacycles. Application to the Synthesis of Polyoxygenated Macrocycles", J. Org. Chem., 1999, pp. 4798-4816.
Doyle et al., "Selectivity in Reactions of Allyl Diazoacetates as a Function of Catalyst and Ring Size from γ-Lactones to Macrocyclic Lactones", J. Org. Chem., 65, 2000, pp. 8839-8847.
Corona et al., "Synthesis of A Biotin-Derived Alkyne for PD-Catalyzed Coupling Reactions", Organic Letters, vol. 8, No. 9, Mar. 31, 2006, pp. 1883-1886.
Delaluz et al., "Synthesis and Use of a Biotinylated 3-Azisophenothiazine to Photolabel Both Amino- and Carboxyl-Terminal Sites in Calmodulin", Bioconjugate Chem., 6, 1995, pp. 558-566.
Galonic et al., "Aziridine-carboxylic Acid-Containing Peptides: Application to Solution and Solid-Phase Convergent Site-Selective Peptide Modification", J. Am. Chem. Soc., 127, 2005, pp. 7359-7369.
Eggins, Chemical Sensors and Biosensors, vol. 3 of Analytical Techniques in the Sciences, 2002, pp. 1-273.
Anderson et al., "Robust Sensing Films for Pathogen Detection and Medical Diagnostics", Proceedings of SPIE, vol. 7167, Frontiers in Pathogen Detection, 2009.
Camarero, "New Developments For The Site-Specific Attachment of Protein To Surfaces", Biophysical Reviews and Letters, vol. 1, No. 1, 2006, pp. 1-28.
"Thermo Scientific Avidin-Biotin Technical Handbook" Thermo Scientific, 2009, p. 1-48.
Sarkar et al., "Addressing Thrombogenicity in Vascular Graft Construction", Journal of Biomedical Materials Research Part B: Applied Biomaterials, Jul. 2007, pp. 100-108.
Del Mel et al., "Surface Modification of Biomaterials: A Quest for Blood Compatibility", International Journal of Biomaterials, Hindawi Publishing Corporation, 2012, vol. 2012, pp. 1-8.
Sheikh et al., "Single ether group in a glycol-based ultra-thin layer prevents surface fouling from undiluted serum", Chem.Commun., Dec. 16, 2011, 48, pp. 1305-1307.
Rjeb et al., "Polypropylene natural aging studied by X-ray photoelectron spectroscopy", Journal of Electron Spectroscopy and Related Phenomena, Jun. 2000, vol. 107, pp. 221-230.
Soraru et al., "XPS characterization of gel-derived silicon oxycarbide glasses", Materials Letters, vol. 27 Issues 1-2, May 1996, pp. 1-5.
Hijikata et al., "Composition analysis of SiO2/SiC interfaces by electron spectroscopic measurements using slope-shaped oxide films", Applied Surface Science, vol. 184, Issues 1-4, Dec. 12, 2001, pp. 161-166.
Jing et al., "Chemical Bond Structure on Si—O—C Composite Films with a Low Dielectric Constant Deposited by Using Inductively Coupled Plasma Chemical Vapor Deposition", Journal of the Korean Physical Society, vol. 41, No. 5, Nov. 2002, pp. 769-773.
Kundu et al., "FTIR Studies of gel to glass conversion in TEOS—fumed silica-derived", Journal of Non-Crystalline Solids, 1993, vol. 155, pp. 253-258.
Ou et al., "Near- and mid-infrared spectroscopy of sol-gel derived ormosils: vinyl and phenyl silicates", Journal of Non-Crystalline Solids, vol. 210, Issues 2-3, Mar. 1997, pp. 187-203.
Silberzan et al., "Silanation of Silica Surfaces. A New Method of Constructing Pure or Mixed Monolayers",Langmuir, Aug. 1991, vol. 7, pp. 1647-1651.
Van Oss, et al., "Interfacial lifshitz—van der Waals and Polar Interactions in Macroscopic Systems", Chem. Rev., Sep. 1988, vol. 88, pp. 927-941.

\* cited by examiner

Scheme 1

Scheme 2

Scheme 3

Scheme 4

Scheme 5

Scheme 6

Scheme 7

MODIFICATION OF BIOMEDICAL POLYMERS FOR PREVENTION OF FOULING AND CLOTTING

CROSS-REFERENCE TO RELATED APPLICATIONS

This application is a continuation in part of U.S. patent application Ser. No. 13/154,067 filed Jun. 6, 2011 entitled: Avoidance Of Non-Specific Binding On An Acoustic Wave Biosensor Using Linker And Diluent Molecules For Device Surface Modification which claims the benefit of and priority to U.S. Provisional Patent Application No. 61/353,383 filed Jun. 10, 2010, entitled: Avoidance of Non-specific Binding on an Acoustic Wave Biosensor Using Linker and Diluent Molecules for Device Surface Modification. Both documents are hereby incorporated by reference in their entirety.

FIELD

The present invention relates generally to polymer surface modification using self-assembled monolayer (SAM) chemistry and to the development of antifouling or fouling resistant surfaces.

BACKGROUND

Polymer-based materials are currently widely employed in many industries including medical, construction and transport. The trend continues to grow as more plastics replace conventional materials such as metal, wood, or glass.

Currently, a significant problem leads to a reduction of equipment efficiency in many industries including medical, transportation and textile: fouling on polymer surfaces. In the medical industry, coating of surfaces has received major interest especially for forming biocompatible materials for equipment coming in direct contact with bodily fluids (i.e. blood, urine). An example of concern is the formation of thrombus in dialysis due to incompatibility with blood components. Thrombus formation occurs from cell aggregation on surface and results in altered flow dynamics, which is a primary reason for failure of blood contacting devices.[30]

Also, formation of thrombus on surface in implantable devices may lead to turbulent flow and other complications inside the patient's body. This leads to several surgeries and post-surgery mortality in patients undergoing treatment.[31] During surgery, many devices currently use polymer-based components that come in contact with blood. Those include tubing, filters, catheters, implants, bypass grafts, vascular stents, heart valves and a wide variety of other parts. Many of these devices require blood compatibility and as a result pose high risk to patients with cardiovascular problems.

Biosensors are analytical devices that are employed for the detection and transduction of biochemical interactions occurring at the sensor-liquid interface.[1] Although one-use structures are common, there is significant interest in devices that produce measurable signals in a real-time, ideally label-free manner. This type of detection technology constitutes a particularly attractive analytical tool that has received increasing attention over recent years with respect to environmental,[2] food,[3] and drug analysis,[4] detection aspects of biochemical warfare,[5] and clinical diagnostics.[6] However, before a biosensor can be implemented as a reliable, commercially viable diagnostic device, there are a number of requirements to be addressed. The attachment of the biosensing element to the transducer must be performed in a highly controlled fashion in terms of surface distribution and spatial orientation. Moreover, biological activity must be retained upon binding[7] in order for the target analyte to interact efficiently with the surface-attached biochemical probe. Further, the device should display both high specificity and sensitivity towards the target analyte and provide reliable and reproducible results, even in the presence of potentially interfering species. The undesired "non-specific adsorption" of adversary species (as opposed to the "specific adsorption" of the target analyte) has been a common and prevailing concern with respect to the analysis of complex biological samples such as blood, serum or urine. Accordingly, considerable attention has been paid to the role of adsorption effects and surface chemistry on biosensor response.

Self-assembling monolayer (SAM) chemistry is regularly regarded as a method of choice for the quick and economical preparation of structurally well-defined and customizable thin organic surfaces.[8] SAM chemistry relies on the use of linking molecules that are engineered to spontaneously form ordered molecular assemblies on solid inorganic substrates.[8] Moreover, functionalizable SAMs can also be designed to immobilize, in a subsequent step, various biomolecules such as proteins,[9] antibodies,[10] or oligonucleotides.[11] Understandably, these attractive properties have endowed SAM chemistry with a unique position for the fabrication of biosensors.[12]

The conversion of biological events into measurable signals requires the development of new transducing technologies that are capable of being interfaced with appropriate surface chemistry in an intimate overall structure. Amongst the various transducing systems and devices that have been engineered, those based on acoustic wave physics that commonly rely on the unique piezoelectric properties of quartz,[13,14] constitute an important, yet arguably underexploited[14] technology for application in the bioanalytical field.[15]

U.S. Pat. No. 7,207,222 entitled "Electromagnetic Piezoelectric Acoustic Sensor" describes a sensor that comprises a piezoelectric sensor plate spaced apart from an induced dynamic electromagnetic field, such as from an electromagnetic coil through which AC current flows. This acoustic wave device, referenced herein as EMPAS, is based on the electromagnetic excitation of higher harmonics in the piezoelectric substrate.[16] In practice, EMPAS offers several major advantages over its predecessors, such as an electrode-free environment and the ability to conduct measurements at tunable, ultra-high frequencies (up to 1.06 GHz), which allows for detailed information and enhances sensitivity.[17]

Following SAM formation, various biomolecules may be immobilized onto a sensor surface in a subsequent step[18] in order to formulate a functionalized surface for an intended application.

The following abbreviations are used herein: ATR: Attenuated total reflectance; CAG: Contact angle goniometry; 7-OEG: 2-(3-trichlorosilyl-propyloxy)-ethyl-trifluoroacetate; CPB: Cardiopulmonary bypass; MEG-OH: Monoethylene glycolated-OH (TFA-deprotected form of 7-OEG on a surface); MEG-TFA: Monoethylene glycolated trifluoroacetyl (7-OEG surface modifier on a surface); OTS: octyltrichlorosilane; OEG-TUBTS: S-(2-(2-(2-(3-trichlorosilyl-propyloxy)-ethoxy)-ethoxy)-ethylbenzenethiosulfonate; PET: Poly(ethylene terephthalate); PC: Polycarbonate; POP: Polypropylene; PUR: Polyurethane; PVC: Polyvinyl chloride; SAM: Self-assembled monolayer; SDS: Sodium dodecyl sulfate; TTTA: 2,2,2-trifluoroethyl-13-trichlorosilyl-tridecanoate; TFA: Trifluoroacetyl; and XPS: X-ray photoelectron spectroscopy.

It is desirable to provide a coating for a polymeric surface that is capable of reducing or minimizing fouling or clotting upon exposure to biological fluids.

SUMMARY

It is an object to obviate or mitigate at least one disadvantage of previous technologies.

Polymeric surfaces having desirable properties are described. A method for forming such surfaces is described. The method involves plasma activation and self-assembling monolayer (SAM) technology on polymer surfaces to form coatings that have antifouling properties, and which may reduce clotting. The method is applicable to polymers that can present hydroxyl groups on the surface. The surface coating involves an organosilane-based SAM that deposits and anchors onto surface hydroxyl groups, forming Si—O bonds. The coating is covalently bound, and thus can be used for prolonged periods of time.

There is described herein a surface-modified polymer comprising a polymeric material and a self-assembling monolayer covalently bound on the surface of the polymeric material, wherein the monolayer comprises monoethylene glycolated-OH (MEG-OH); 2-(3-trichlorosilyl-propyloxy)-ethyl-trifluoroacetate (7-OEG or MEG-TFA); 2,2,2-trifluoroethyl-13-trichlorosilyl-tridecanoate (TTTA); OEGylated TTTA (OEG-TTTA); S-(2-(2-(2-(3-trichlorosilyl-propyloxy)-ethoxy)-ethoxy)-ethyl)-benzenethiosulfonate (OEG-TUBTS); or a combination thereof.

Furthermore, there is described herein a method of forming a surface-modified polymer having a self-assembling monolayer thereon, the method comprising: activating the surface of the polymeric material to generate hydroxyl groups thereon and silanizing the activated surface with a monolayer comprising monoethylene glycolated-OH (MEG-OH); 2-(3-trichlorosilyl-propyloxy)-ethyl-trifluoroacetate (7-OEG or MEG-TFA); 2,2,2-trifluoroethyl-13-trichlorosilyl-tridecanoate (TTTA); OEGylated TTTA (OEG-TTTA); S-(2-(2-(2-(3-trichlorosilyl-propyloxy)-ethoxy)-ethoxy)-ethyl)-benzenethiosulfonate (OEG-TUBTS); or a combination thereof.

Additionally, there is described herein a method of preventing or reducing fouling of a polymer upon contact with a biological fluid, comprising modifying the surface of the polymer with a covalently bound self-assembling monolayer, wherein the monolayer comprises monoethylene glycolated-OH (MEG-OH); 2-(3-trichlorosilyl-propyloxy)-ethyl-trifluoroacetate (7-OEG or MEG-TFA); 2,2,2-trifluoroethyl-13-trichlorosilyl-tridecanoate (TTTA); OEGylated TTTA (OEG-TTTA); S-(2-(2-(2-(3-trichlorosilyl-propyloxy)-ethoxy)-ethoxy)-ethyl)-benzenethiosulfonate (OEG-TUBTS); or a combination thereof, and wherein the polymer is formed of a polymeric material having hydroxyl groups thereon, comprising polycarbonate, poly(ethylene terephthalate), polypropylene, polyvinyl chloride, polyurethane, poly(methyl methacrylate), nylon, polyethylene or combinations thereof.

The use of a surface so coated can advantageously result in a reduction of thrombus formation from the polymer surface. The technology has application in the field of biomedical polymers, where surface fouling and clot formation are undesirable and/or problematic.

Described herein is a method of forming a surface that could be used to modify polymers in a manner that reduces fouling.

Other aspects and features will become apparent to those ordinarily skilled in the art upon review of the following description of specific embodiments in conjunction with the accompanying figures.

BRIEF DESCRIPTION OF THE DRAWINGS

Embodiments will now be described, by way of example only, with reference to the attached Figures.

DETAILED DESCRIPTION

The coating of polymeric materials with surface-modifying molecules to impart antifouling and anti-adhesion properties is described. The self-assembling monolayer (SAM) principle is utilized. The coating comprises a SAM made of molecules having a highly reactive trichlorosilane anchoring function. The monolayer may include a single type of trichlorosilane molecule, or multiple types of such molecules, optionally with a shorter diluent molecule. A monolayer having such molecules as a 2-(3-trichlorosilyl-propyloxy)-ethyl-trifluoroacetate (7-OEG or MEG-TFA), which can self-assemble on hydroxyl groups present on surfaces, is an exemplary type of monolayer for coating the surface of the polymeric material.

Figure 9:
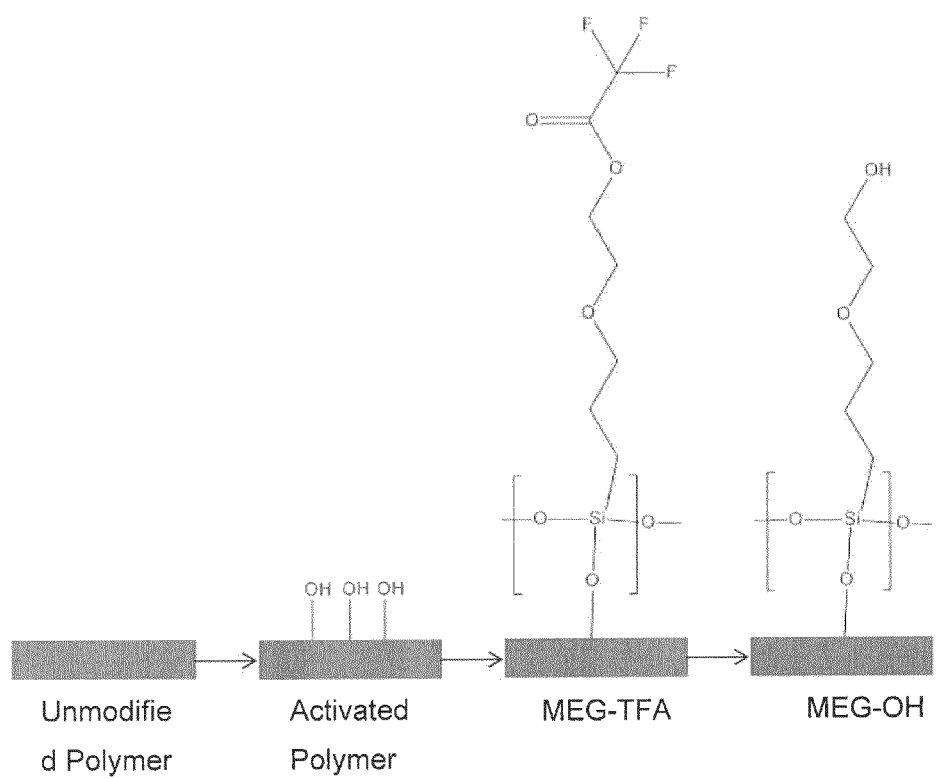
FIG. 9 illustrates a generalized surface modification for application to polymers having or capable of being converted to hydroxyl groups. Step 1) involves plasma activation, step 2) involves deposition of MEG-TFA onto the surface, and step 3) involves conversion of MEG-TFA to MEG-OH.

The deposited molecule in the monolayer can be activated to form an antifouling surface, for example by removing the TFA group and form a hydroxyl group on the surface, such as depicted in FIG. 9. The modified surface can then be brought into contact with complex liquids that may be expected to cause fouling, without experiencing fouling to the extent seen on uncoated surfaces.

Currently, most medical equipment contacting biological fluids is produced from polymer materials. Continuous contact with these fluids results in unwanted chemical interactions, potentially leading to complications during or after the medical procedure. To address this ubiquitous fouling problem, antifouling coatings are described herein, which are based on the surface chemistry of short trichlorosilane surface modifiers. The procedure allows for films to be deposited onto several common plastics used in the medical industry including poly(ethylene terephthalate), polycarbonate, polypropylene, polyvinyl chloride, and polyurethane. Adlayer formation is characterized herein using contact angle goniometry (CAG), attenuated total reflectance infrared spectroscopy (ATR-IR) and X-ray photoelectron spectroscopy (XPS). Efficiency of the surface coating is analyzed herein using fluorescence microscopy for platelet adhesion and aggregation.

Surface modification of the polymer substrates according to the method described herein results in surfaces with antifouling properties.

The method described can be applied to a wide variety of polymers that can be activated using plasma. Exemplary surface materials include poly(ethylene terephthalate) (PET), polycarbonate (PC), polypropylene (POP), polyvinyl chloride (PVC), polyurethane (PUR), poly(methyl methacrylate), nylon, polyethylene, and any polymer that could present hydroxyl groups on its surface using plasma.

Polymers for use with the method described herein may be organic-type polymers having carbon and hydrogen content, with a partial or full carbon backbone. Other common elements may be contained in the polymers, such as nitrogen, oxygen, fluorine and chlorine. Other types of less common atoms may be used/found in the polymers. The polymer should be one that is able to present hydroxylated groups. All polymers used in the method should include carbon and hydrogen in the backbone. Polymer mixtures can be used if the mixture contains the organic-type backbone in one of the polymers. Branched polymers are also suitable for the method described herein.

A surface-modified polymer is described, which comprises a polymeric material and a self-assembling monolayer covalently bound on the surface of the polymeric material. The monolayer may comprise one or more of monoethylene glycolated-OH (MEG-OH); 2-(3-trichlorosilyl-propyloxy)-ethyl-trifluoroacetate (also referred to herein as: "7-OEG" or "MEG-TFA", interchangeably); 2,2,2-trifluoroethyl-13-trichlorosilyl-tridecanoate (TTTA); OEGylated TTTA (OEG-TTTA); S-(2-(2-(2-(3-trichlorosilyl-propyloxy)-ethoxy)-ethoxy)-ethyl)-benzenethiosulfonate (OEG-TUBTS); or other similar materials capable of forming a monolayer in a similar manner. In an exemplary embodiment, the monolayer may additionally comprise one or more additional molecules, such as shorter diluent molecules. An exemplary additional molecule is octyltrichlorosilane (OTS).

The monolayer may comprise MEG-TFA.

The monolayer may comprise MEG-OH.

The monolayer may comprise a mixture of TTTA and OTS.

The monolayer may comprise a mixture of OEG-TTTA and 7-OEG.

The monolayer may comprise a mixture of OEG-TUBTS and 7-OEG.

The polymer as modified in a manner described herein may comprise, as the unmodified starting material, any polymeric material comprising available hydroxyl groups, or which may be functionalized to possess available hydroxyl groups. Exemplary polymeric materials include polycarbonate, poly (ethylene terephthalate), polypropylene, polyvinyl chloride, polyurethane, poly(methyl methacrylate), nylon, polyethylene, or combinations thereof. Polycarbonate is an exemplary material from which the polymer may be made.

A method of forming a surface-modified polymer having a self-assembling monolayer thereon is described. The method comprises: activating a surface of a polymeric material with hydroxyl groups thereon and silanizing the activated surface with a monolayer. In the method described, the monolayer comprises monoethylene glycolated-OH (MEG-OH); 2-(3-trichlorosilyl-propyloxy)-ethyl-trifluoroacetate (7-OEG or MEG-TFA); 2,2,2-trifluoroethyl-13-trichlorosilyl-tridecanoate (TTTA); OEGylated TTTA (OEG-TTTA); S-(2-(2-(2-(3-trichlorosilyl-propyloxy)-ethoxy)-ethoxy)-ethyl)-benzenethiosulfonate (OEG-TUBTS); or may include a combination of these, with or without a diluent molecule. The activation of the surface may comprise exposing the surface to a plasma.

The monolayer may additionally comprise octyltrichlorosilane (OTS), or another molecule or diluent that permits a monolayer to form.

In the method described herein, the polymeric material may comprise polycarbonate, poly(ethylene terephthalate), polypropylene, polyvinyl chloride, polyurethane, poly(methyl methacrylate), nylon, polyethylene, or combinations thereof. Other polymers may be included.

A method of preventing or reducing fouling of a polymer upon contact with a biological fluid is described herein. The method comprises modifying the surface of the polymer with a covalently bound self-assembling monolayer. The monolayer may include monoethylene glycolated-OH (MEG-OH); 2-(3-trichlorosilyl-propyloxy)-ethyl-trifluoroacetate (7-OEG or MEG-TFA); 2,2,2-trifluoroethyl-13-trichlorosilyl-tridecanoate (TTTA); OEGylated TTTA (OEG-TTTA); S-(2-(2-(2-(3-trichlorosilyl-propyloxy)-ethoxy)-ethoxy)-ethyl)-benzenethiosulfonate (OEG-TUBTS); or a combination thereof. The polymer is formed of a polymeric material having hydroxyl groups thereon, or which is capable of being modified to possess hydroxyl groups thereon, comprising polycarbonate, poly(ethylene terephthalate), polypropylene, polyvinyl chloride, polyurethane, poly(methyl methacrylate), nylon, polyethylene or combinations thereof.

Preventing or reducing fouling may involve preventing or reducing thrombus or clot formation, the biological fluid being blood. The method and modified polymers described herein may have particularly advantageous applications in equipment used for cardiac dialysis, especially on inner luminal surfaces of tubes through which blood circulates out of and back into an individual. While blood thinners can be used to prevent micro-clotting, it is nevertheless advantageous to have equipment that is resistant to formation of thrombus and clot formation of any kind. Equipment and tubing commonly used in applications where exposure to blood is common can benefit from surface modification according to the method described herein.

Cardiopulmonary bypass (CPB) during surgery is used in a wide variety of surgeries. During the process, blood is required to leave the body, generally via polymeric tubing. Thus, a patient's blood comes into contact with polymeric surface. As a result of this contact, interactions between blood and the polymer surface can occur, including platelet adhesion, aggregation and activation, protein configuration changes, affinity for and/or binding of other proteins including fibrinogen or albumin, and endothelial cell receptor binding to ligands. Such reactions may modify the polymeric surface to form aggregates thereon. Thrombus formation on the polymeric surface may lead to turbulent flow through equipment or tubing leading to complications. Furthermore, small clots or other aggregates formed on such surfaces, which may circulate back into the body as a result of the bypass could lead to complications such as blockages resulting in stroke. Such complications may be avoided if the polymeric surface was to be modified in a manner that discouraged "fouling" (which encompasses aggregation, clotting, and other surface binding or interactions) as with the modified surface described herein.

Generally, there is provided an acoustic wave biosensor comprising a surface of a mixed self-assembling monolayer for receiving a biomolecule. The biosensor surface comprises a piezoelectric quartz crystal surface with a mixed self-assembling monolayer (SAM). The mixed self-assembling monolayer can include 2,2,2-trifluoroethyl-13-trichlorosilyl-tridecanoate (TTTA); OEGylated TTTA (OEG-TTTA); S-(2-(2-(2-(3-trichlorosilyl-propyloxy)-ethoxy)-ethoxy)-ethyl)-benzenethiosulfonate (OEG-TUBTS) linker.

A linker/diluent system can be used in which the diluent may comprise octadecyltrichlorosilane (OTS) or 2-(3-trichlorosilyl-propyloxy)-ethyl-trifluoroacetate (7-OEG). Exemplary linker/diluent systems include TTTA/OTS, OEG-TTTA/7-OEG, or OEG-TUBTS/7-OEG.

The surface of the biosensor may be subsequently functionalized for analyte detection. Functionalization may involve a biotin derivative, such as biotinthiol.

Oligoethylene glycol linkers are described herein for attaching a functionalizing entity to the surface of a biosensor, for example OEG-TTTA/7-OEG, or OEG-TUBTS/7-OEG may be used.

A method for preparing a biosensor surface is described herein, which comprises preparing the surface to receive a self-assembling monolayer, followed by assembly of the monolayer thereon. Exemplary surfaces may include TTTA/OTS, OEG-TTTA/7-OEG, or OEG-TUBTS/7-OEG.

EXAMPLES

Exemplary embodiments are described below.

Example 1

OligoEthylene Glycol Linkers for the Surface Modification of an Ultra-High Frequency Acoustic Wave Biosensor The following exemplary embodiments describe the application of EMPAS acoustic wave technology for the real-time and label-free surface detection of biotin-avidin interactions. Biosensing surfaces are constructed onto unelectroded piezoelectric quartz discs as functionalizable mixed self-assembled monolayers (SAM) produced from previously unreported linker and diluent molecules. Biotinthiol can subsequently be immobilized for detection purposes in a straightforward and coupling-free manner. Specific and non-specific adsorptions of avidin are measured at tunable, ultra-high frequencies (1.06 and 0.82 GHz) with an electromagnetic piezoelectric acoustic sensor (EMPAS) using micromolar avidin-spiked buffer solutions. These biosensing surfaces, especially the oligoethylene glycol SAM-based variety, display high specificity for avidin, with moderate to excellent reproducibility. This work constitutes the first application of SAM chemistry and EMPAS technology in the bioanalytical field.

Methodology

The following includes detailed protocols for quartz disc cleaning, mixed SAM formation, biotinthiol immobilization and EMPAS measurements. Anhydrous toluene for SAM formation and freshly distilled anhydrous DMF (from $CaH_2$, under high vacuum) or spectrograde MeOH for biotinthiol immobilization were systematically used. Octadecyl-trichlorosilane (OTS) was distilled and stored in carefully sealed vials prior to use. $Et_3N$ was distilled from KOH. Avidin (from egg white, lyophilized powder) and Dulbecco's phosphate buffered saline (PBS) were purchased from Sigma-Aldrich®. Quartz crystals (AT-cut, 13.5 mm or 7 mm in diameter, 20 MHz fundamental frequency) were purchased from Lap-Tech Inc.®. Quartz crystal silanization (SAM formation) and biotinthiol immobilization reactions were prepared in a glovebox maintained under an inert ($N_2$) and anhydrous ($P_2O_5$) atmosphere. The crystals were systematically handled with thoroughly pre-cleaned stainless steel tweezers in order to minimize any external contamination. EMPAS measurements were performed at either 1.06 GHz (53rd harmonic) or 0.82 GHz (41st harmonic).

Avidin is well-known for exhibiting very high affinity towards biotin (Ka~$10^{15}$ M$^{-1}$). This feature made the biotin-avidin system a valuable model for testing the viability of our biosensors. The interactive biotinyl residue was introduced onto the mixed SAMs upon immobilization of our probe-biomolecule, biotinthiol. For a comprehensive handbook on the biotin-avidin chemistry and its various applications in the bioanalytical field, see: Savage et al., 1992.[19]

Quartz Crystal Cleaning Procedure.

Quartz crystals (13.5 and 7 mm in diameter) were first sonicated in 20 mL of concentrated dishwashing soap for 30 minutes. The crystals were then thoroughly rinsed with hot water followed by distilled water then gently dried with forced air. Subsequently, the crystals were individually soaked in 6 mL of Piranha solution (3:1 (v/v) mixture of $H_2SO_4$ and 30% $H_2O_2$) pre-heated to 90° C. using a water bath (CAUTION: Piranha solutions are dangerous, and are to be handled with care). After 30 minutes, the crystals were rinsed with distilled water (3×) followed by spectrograde methanol (3×). Next, the crystals were sonicated in spectrograde methanol for 2 min then individually transferred into vials, which were subsequently placed in an oven maintained at 150° C. for drying. After 2 hours, the vials were immediately transferred into a humidity chamber, maintained at 60% relative humidity using a saturated solution of $MgNO_3.6H_2O$, and set aside overnight.

Silanization Procedure (SAM Formation).

Neat linker (TTTA, OEG-TTTA or OEG-TUBTS, 10 µL) and neat diluent (OTS or 7-OEG, 10 µL) were separately diluted with anhydrous toluene (10 mL). 500 µL of each solution were mixed in individual test tubes into which cleaned quartz crystals were then soaked. The test tubes were sealed with rubber stoppers, removed from the glovebox, and placed on a spinning plate for 2 h. The crystals were then rinsed twice with dry toluene and finally sonicated in toluene for 5 minutes. After a final rinse with one portion of toluene, the previous procedure was repeated with dry chloroform. Finally, the crystals were rinsed twice with dry chloroform, gently dried under forced air then individually transferred into vials for storage (SAM characterization or EMPAS controls) or immediately engaged in the subsequent biotinthiol immobilization procedure (EMPAS samples).

Immobilization of Biotinthiol.

Biotinthiol solutions (1.0 mg/mL) for immobilization onto TTTA/OTS or OEG-TTTA/7-OEG mixed SAMs were prepared by dissolving biotinthiol into freshly distilled DMF. Biotinthiol solutions (1.0 mg/mL) for immobilization onto OEG-TUBTS/7-OEG mixed SAMs were prepared by dissolving biotinthiol into MeOH or a 1/1 (v/v) MeOH/$H_2O$ mixture, to which Et$_3$N (1 µL per mL of solvent) was also added. These solutions were portioned (1 mL) in dry test tubes into which freshly prepared mixed SAM-coated quartz crystals were soaked. The test tubes were sealed with rubber stoppers, removed from the glovebox and placed on a spinning plate overnight. The crystals were then rinsed three times with spectrograde methanol, dried under a gentle N$_2$ stream then finally placed into screw cap vials under atmospheric conditions for EMPAS analysis.

EMPAS Measurements.

Avidin solutions (1.0 mg/mL) were prepared by dissolving 1.0 mg of solid avidin into 1 mL of PBS buffer. After the standard set-up of EMPAS,[17] biotinylated (or non-biotinylated) mixed SAM-coated quartz crystals were individually inserted into the flow through cell and PBS buffer was flown at a rate of 50 µL/min. Once the frequency signal stabilized, 50 µL of a freshly prepared 0.1 mg/mL avidin-spiked PBS solution (90 µL of PBS buffer+10 µL of 1.0 mg/mL avidin) were injected into the flow through system using a low-pressure chromatography valve. Once the avidin-spiked PBS solution completely passed over our surface, the uninterrupted PBS buffer flow rinsed the surface of any loosely bound material. The frequency signal stabilized again, the experiment was stopped and the frequency shift (for specific or non-specific avidin adsorption) was calculated.

Results and Discussion

Figure 1:
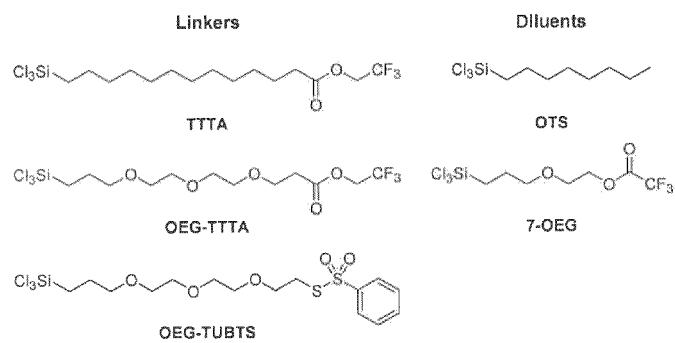
FIG. 1 illustrates schemes relevant to the Examples. Scheme 1 illustrates linker and diluent chemical structures, while Scheme 2 illustrates the formation of a mixed SAM onto a cleaned quartz crystal (step I) and the subsequent site-specific covalent immobilization of biotinthiol (step II): example with the TTTA/OTS linker/diluent system. OEG-TTTA/7-OEG and OEG-TUBTS/7-OEG systems follow the same scheme.
Figure 1:
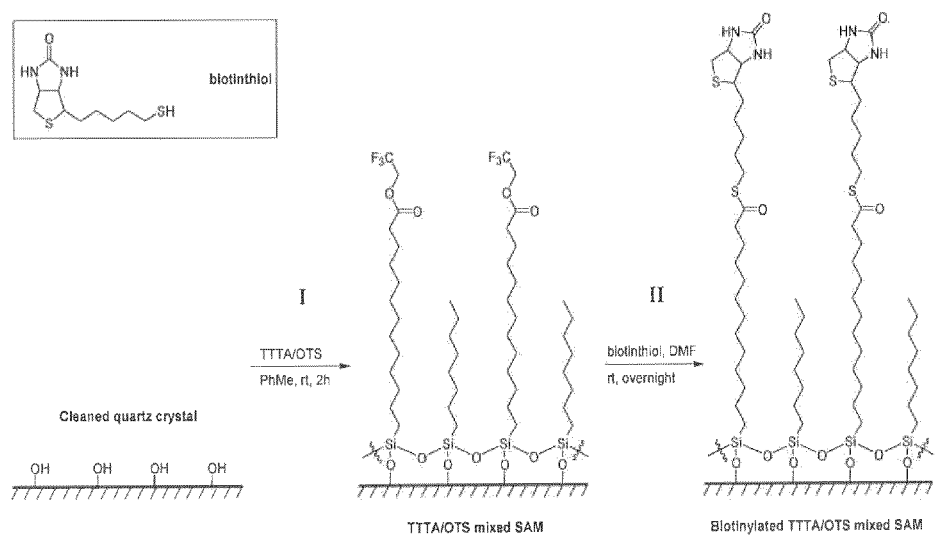

The strategy first involved the preparation of robust and durable mixed SAMs onto hydroxylated AT-cut quartz discs using, in conjunction, combinations of unreported trichlorosilane linker and diluent molecules (FIG. 1, Scheme 1). Scheme 1 illustrates linker and diluent chemical structures. Both linkers and diluents possess a highly reactive trichlorosilyl tail function (Cl$_3$Si—), for strong and robust covalent anchorage onto the underlying hydroxylated quartz surfaces,[20] and an organic backbone to drive self-assembly and provide stability, rigidity and ordering to the mixed SAMs through intermolecular interactions.[8c] Linkers also possess reactive functionalizable head functions (trifluoroethyl ester (TFEE) or benzothiosulfonate (BTS)) for the subsequent site-specific covalent immobilization of a probe-biomolecule, biotinthiol (FIG. 1, Scheme 2), onto the mixed SAMs. Scheme 2 illustrates the formation of a mixed SAM onto a cleaned quartz crystal (step I) and the subsequent site-specific covalent immobilization of biotinthiol (step II): example with the TTTA/OTS linker/diluent system. OEG-TTTA/7-OEG and OEG-TUBTS/7-OEG systems follow the same scheme. Diluents are shorter molecules where the purpose is to space out linker molecules within otherwise inherently denser and congested "undiluted" assemblies.[21] This strategy decreases steric hindrance around neighboring linker head functional groups. As a result, mixed SAMs were anticipated to offer enhanced binding ability (better reactivity and accessibility) for biomolecule immobilization and to facilitate access with regard to target analyte binding.[7a, 9, 12a-c, 22]

Three types of mixed SAMs (TTTA/OTS, OEG-TTTA/7-OEG, and OEG-TUBTS/7-OEG) were successfully prepared upon immersion of cleaned quartz discs (13.5 or 7 mm in diameter) into the appropriate 1/1/2000 (v/v/v) linker/diluent solutions in anhydrous toluene, for 2 h at room temperature (FIG. 1, Scheme 2, step I). Mixed SAM characterization was achieved using contact angle goniometry (Table 1) and angle-resolved X-ray photoelectron spectroscopy (as outlined below in section entitled "Supporting Information"). These SAMs were then biotinylated in a single, straightforward, and coupling-free step, upon immersion into 1.0 mg/mL solutions of biotinthiol in anhydrous DMF or MeOH, overnight at room temperature (FIG. 1, Scheme 2, step II).

TABLE 1

Static contact angle measurements for TTTA/OTS, OEG-TTTA/7-OEG and OEG-TUBTS/7-OEG mixed SAMs recorded with ultrapure water

| Surface | Contact angle |
| --- | --- |
| TTTA/OTS SAM | 77° |
| OEG-TTTA/7-OEG SAM | 69° |
| OEG-TUBTS/7-OEG SAM | 75° |
| Cleaned quartz disc | 12° |

For each linker/diluent system, EMPAS experiments involved two sets of independent frequency shift measurements (4 to 6 replicates per set), that were conducted at 1.06 GHz (13.5 mm discs) or 0.82 GHz (7 mm discs) using 0.1 mg/mL solutions of avidin in phosphate buffer saline (PBS). On the one hand, biotinylated mixed SAMs (samples) were dedicated to record specific adsorption of avidin to biotin. On the other hand, non-biotinylated mixed SAMs constituted controls that were dedicated to quantify non-specific adsorption of avidin. Specific to non-specific adsorption frequency shift ratios ($R_{S/NS}$) and relative standard deviations (RSD) were then calculated to assess the efficiency of our biosensing surfaces to specifically detect avidin and the reproducibility of our measurements, respectively.

The TTTA/OTS system was first investigated on 13.5 mm discs (FIG. 2) which resulted in very encouraging results since the specific adsorption frequency shifts (15 kHz) were significantly larger than the ones recorded for non-specific adsorption (4 kHz). In each of the three pairings of bars shown in FIG. 2, the first of the two bars (lighter grey) is indicative of specific adsorption, whereas the second bar (darker grey) represents non-specific adsorption. For TTTA/OTS, $R_{S/NS}$ (13.5 mm discs)=3.8/1; for OEG-TTTA/7-OEG $R_{S/NS}$=6.3/1, and for OEG-TTA/7-OEG (7 mm discs) $R_{S/NS}$=4.1/1. The resulting $R_{S/NS}$ was excellent (3.8/1) and clearly demonstrating the ability of this system to detect avidin with high specificity. Reproducibility of measurements was reasonable for specific adsorption (RSD=14%). For non-specific adsorption, RSD=39%.

Figure 2:
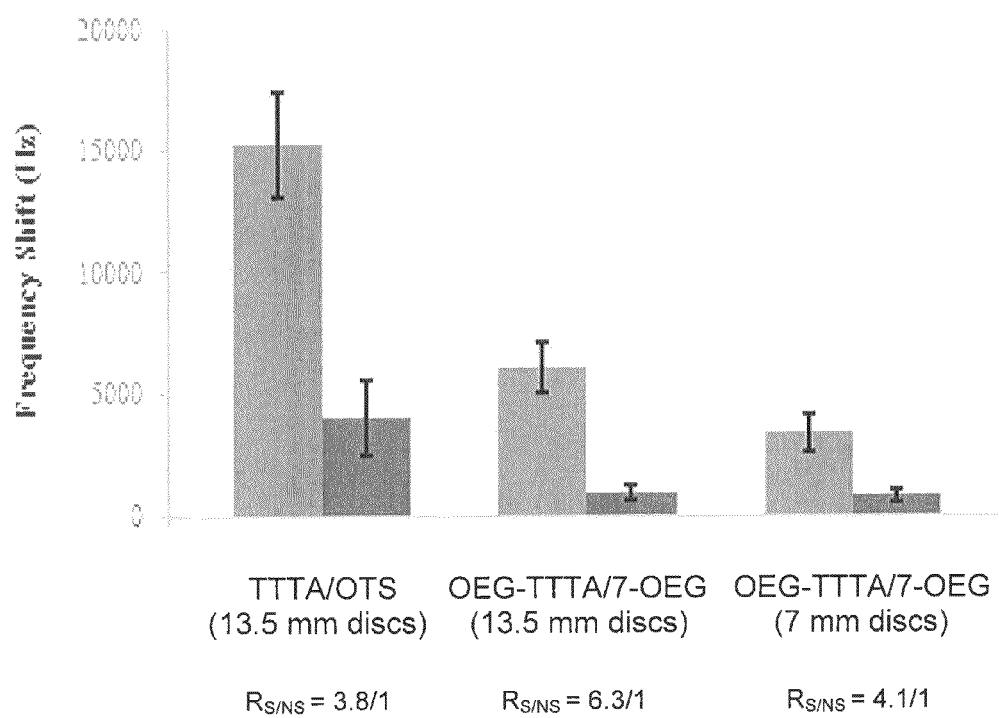
FIG. 2 illustrates EMPAS specific (light grey) and non-specific (dark grey) avidin adsorption frequency shifts respectively measured with biotinylated and non-biotinylated TTTA/OTS and OEG-TTTA/7-OEG mixed SAMs, using 0.1 mg/mL avidin-spiked PBS solutions. EMPAS measurements were recorded at 1.06 GHz for the 13.5 mm discs and at 0.82 GHz for the 7 mm discs.

In order to improve the performance of the system with respect to specific vs. non-specific adsorption, we next prepared OEG-TTTA/7-OEG mixed SAMs, TTTA/OTS mixed SAM analogs that possess oligoethylene glycol (OEG) backbones. This choice was motivated by the fact that OEGylated SAMs have been reported to act as non-fouling surfaces that successfully resist undesired non-specific adsorption,[23] a remarkable property that is currently drawing much attention in the bioanalytical field.[21,24] This approach is highly successful since OEG-TTTA/7-OEG mixed SAMs did indeed allow us to substantially improve the performance of our device (with a $R_{S/NS}$ now reaching 6.3/1), confirming the general observation that OEGylated SAMs exhibit non-fouling properties (FIG. 2, exp. 2). The reproducibility of the measurements for specific and non-specific adsorptions was found to be (RSD values) 16% and 33%, respectively. In view of the current trend towards biosensor miniaturization and in order to make our device even more attractive for future applications, next was prepared OEG-TTTA/7-OEG mixed SAMs on 7 mm discs—i.e. on surface areas four times smaller than those of the 13.5 mm discs (38 $mm^2$ vs. 142 $mm^2$). This new experiment (FIG. 2, exp. 3) was a success and provided an excellent yet slightly lower $R_{S/NS}$ of 4.1/1, indicating that our OEG-TTTA/7-OEG biosensing platforms could be considerably miniaturized while still maintaining high specificity for avidin. Reproducibility was shown to be RSD=23% for specific and RSD=33% for non-specific adsorptions.

As observed for the experimental results discussed above, the reproducibility of measurements constituted a limitation to our otherwise highly performing TFEE biosensing surfaces. It was hypothesized that low reproducibility values essentially reflect the fact that the biosensing surfaces of a same series, although prepared under identical conditions, likely display different linker/diluent compositions and distributions, surface morphologies, and/or biotinthiol loadings; i.e. discrepancies in binding affinity for avidin. In order to better control biotinthiol loadings, a new generation of linkers was next sought, which was able to reliably immobilize biotinthiol. Eventually OEG-TUBTS linker was synthesized (FIG. 1, Scheme 1), an OEGylated molecule that possesses a benzothiosulfonate (BTS) moiety known to readily and chemoselectively react with thiols to form disulfide bonds.[25] BTS functions also tolerate aqueous and alcoholic media,[25] which is particularly appreciable when probe-biomolecules are not soluble into aprotic organic solvents. It is also important to note that despite these remarkable properties, BTS-based molecules have never been involved within SAM chemistry or for the development of biosensors.

Figure 3:
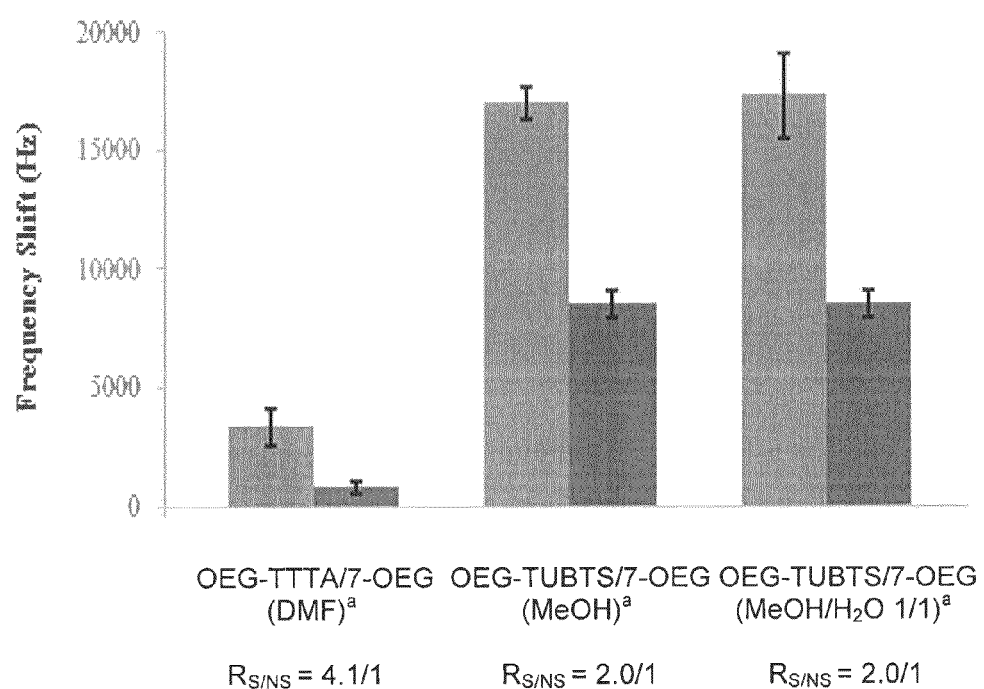
FIG. 3 illustrates EMPAS specific (light grey) and non-specific (dark grey) avidin adsorption frequency shifts respectively measured with biotinylated and non-biotinylated OEG-TUBTS/7-OEG mixed SAMs, using 0.1 mg/mL avidin-spiked PBS solutions, and comparison with the OEG-TTTA/7-OEG system. EMPAS measurements were recorded at 0.82 GHz on 7 mm discs.

FIG. 3 illustrates EMPAS specific (light grey) and non-specific (dark grey) avidin adsorption frequency shifts respectively measured with biotinylated and non-biotinylated OEG-TUBTS/7-OEG mixed SAMs, using 0.1 mg/mL avidin-spiked PBS solutions, and comparison with the OEG-TTTA/7-OEG system. EMPAS measurements were recorded at 0.82 GHz on 7 mm discs. Superscript[a] indicates solvent(s) used for biotinthiol immobilization. We first investigated OEG-TUBTS/7-OEG mixed SAMs (on 7 mm discs, at 0.82 GHz) for which biotinthiol had been immobilized in MeOH as the solvent (FIG. 3, exp. 2). These also exhibited the ability to detect avidin but with lower specificity ($R_{S/NS}$ of 2.0/1) compared to the corresponding TFEE SAMs (FIG. 3, exp. 1). Reproducibility was excellent, for both specific (RSD=4%) and non-specific (RSD=6%) adsorptions.

It is also interesting to note that, in comparison with the TFEE OEGylated mixed SAMs, both reproducibility and frequency shift intensities were considerably greater. For non-specific adsorption, this seems to indicate that BTS OEGylated mixed SAMs are more uniform and display comparatively higher affinity for avidin. With respect to specific adsorption, this strongly supports a higher, more reliably controlled and homogeneous site-specific biotinthiol coverage. Finally, it was necessary to determine whether specific adsorption is affected by immobilizing biotinthiol under mild aqueous conditions. For that purpose, we biotinylated OEG-TUBTS/7-OEG mixed SAMs in a 1/1 (v/v) MeOH/$H_2O$ mixture (Biotinthiol is poorly soluble in water). It is noteworthy that neither the $R_{S/NS}$ (still 2.0/1) nor the RSD value for specific adsorption (10%) were significantly modified (FIG. 3, exp. 3), demonstrating that biotinthiol can also be reproducibly immobilized in an aqueous solvent mixture without altering the performance of the EMPAS biosensor.

Conclusion

This Example presents the construction of several novel, highly performing mixed SAM-based piezoelectric biosensors able to detect biotin-avidin interactions in a real-time and label-free manner using the electromagnetic piezoelectric acoustic sensor (EMPAS). This work constitutes the first application of SAM chemistry and EMPAS technology in the bioanalytical field. Biosensing surfaces were built onto piezoelectric AT-cut quartz discs as robust, durable and functionalizable mixed SAMs—using previously unreported trichlorosilane linker and diluent molecules—onto which biotinthiol could subsequently immobilize in a single, straightforward, and coupling-free step through TFEE or unprecedented BTS head functions. The biosensing properties of these assemblies, in terms of specific and non-specific avidin adsorptions, were measured with EMPAS at ultra-high frequencies (1.06 and 0.82 GHz) using micromolar avidin-spiked PBS buffer solutions. With respect to TFEE head function, biotinylated mixed SAMs efficaciously bound avidin, whereas non-biotinylated ones only exhibited limited binding affinities for avidin. Specific to non-specific avidin adsorption ratios were excellent and systematically improved with OEGylated mixed SAMs but the low reproducibility of our measurements was a recurrent problem. In comparison, BTS OEGylated mixed SAMs exhibited excellent reproducibility but lower specificity towards avidin. During this study, we also showed that the overall biosensing platform could be reduced in size while still maintaining high specificity for avidin (TFEE system) and that biotinthiol immobilization could also be performed under mild aqueous conditions without altering the performance of the sensor (BTS system). Research attention is currently focused on developing OEGylated mixed SAMs that would combine the high specificity displayed by TFEE systems and the excellent reproducibility obtained with BTS OEGylated mixed SAMs. It is also planned to progress from using simple buffered target analyte solutions to complex biological fluids such as serum, urine and blood in a real-world scenario. In these sample matrices, target analytes will be present at low concentration and will have to be distinguished from relatively high concentrations of competing species.

Supporting Information

General Remarks.

The following includes synthetic procedures and characterization data for linker, diluent and biotinthiol molecules as well as contact angle goniometry and X-ray photoelectron microscopy data for SAM characterization. $H_2PtCl_6.6H_2O$ (99.9%) was purchased from Strem Chemicals Inc.®. Other chemicals were purchased from Sigma-Aldrich® and used as received unless otherwise noted. $^1H$ and $^{13}C$ NMR spectra were recorded at room temperature on Varian Mercury 300 or 400 MHz spectrometers using $CDCl_3$ or $CD_3OD$ as the NMR solvents. $^1H$ and $^{13}C$ NMR spectra are referenced to the residual solvent peak ($CDCl_3$: 7.27 ppm ($^1H$) and 77.23 ppm ($^{13}C$), $CD_3OD$: 3.31 ppm ($^1H$)).

TTTA Synthesis

Figure 4:
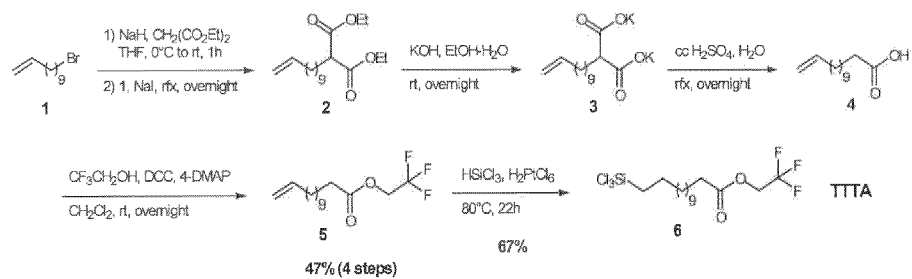
FIG. 4 illustrates Scheme 3, depicting TTTA synthesis.

FIG. 4 illustrates Scheme 3, depicting TTTA synthesis. TTTA (6) was synthesized in five steps from 11-bromo-undec-1-ene (1) with a 31% overall yield.

2,2,2-trifluoroethyl tridec-12-enoate (5)

To a stirred solution of NaH (60%, 484 mg, 12.1 mmol, 1.1 equiv.) in THF (50 mL) was added dropwise diethylmalonate (2.02 mL, 13.2 mmol, 1.2 equiv.) at 0° C. After addition, the reaction was allowed to warm to room temperature then stirred for 1 h. 11-bromo-undec-1-ene (1) (2.54 mL, 11.0 mmol, 1.0 equiv.) and anhydrous NaI (1.65 g, 11.0 mmol, 1.0 equiv.) were then successively added. After refluxing overnight, the reaction was quenched with brine then extracted with EtOAc. The combined organic layers were dried over anhydrous $Na_2SO_4$, filtered then evaporated under reduced pressure to provide crude diethyl malonate (2). The latter was diluted with a 1/1 (v/v) mixture of EtOH (20 mL) and 2.6 M KOH aqueous solution (20 mL). The reaction was vigorously stirred at room temperature overnight then the solvents were evaporated under reduced pressure to provide crude dipotassium malonate (3). The residue was then submitted to a $H_2O$/$CH_2Cl_2$ extraction. The combined aqueous layers were concentrated under reduced pressure to about 100 mL then carefully acidified with concentrated $H_2SO_4$. The reaction was refluxed overnight then submitted to a $CH_2Cl_2$/$H_2O$ extraction. The combined organic layers were dried over anhydrous $Na_2SO_4$, filtered then evaporated under reduced pressure to provide crude acid (4). The latter (2.06 g, 9.70 mmol, 1.0 equiv.) was dissolved in $CH_2Cl_2$ (70 mL) then DCC (2.22 g, 10.7 mmol, 1.1 equiv.), 2,2,2-trifluoroethanol (0.78 mL, 10.7 mmol, 1.1 equiv.) and 4-DMAP (0.12 g, 1.0 mmol, 0.1 equiv.) were successively added. The reaction was stirred at room temperature overnight then filtered through a short plug of Celite ($CH_2Cl_2$ washings). After evaporation of the filtrate under reduced pressure, the final purification was achieved by column chromatography on silica gel (Hexanes/EtOAc gradient) and provided 1.53 g (47%, 4 steps) of ester (5) as a pale yellow oil; $^1H$ NMR (400 MHz, $CDCl_3$) δ 5.81 (m, 1H), 4.99 (m, 1H), 4.93 (m, 1H), 4.47 (q, J=8.4 Hz, 2H), 2.41 (t, J=7.5 Hz, 2H), 2.04 (m, 2H), 1.64 (m, 2H), 1.32 (m, 14H); $^{13}C$ NMR (75 MHz, $CDCl_3$) δ 172.3, 139.4, 123.2 (q, J=275.5 Hz), 114.3, 60.3 (q, J=36.4 Hz), 34.0, 33.8, 29.8, 29.7, 29.6, 29.4, 29.3, 29.2, 29.1, 24.9; IR (neat) 1760 cm$^{-1}$; HRMS (EI, m/z) calcd. for $C_{15}H_{25}O_2F_3$ (M$^{+•}$) 294.1807, found 294.1806.

2,2,2-Trifluoroethyl 13-Trichlorosilyl-TridecAnoate (TTTA) (6)

In a heavy-walled tube equipped with a magnetic stir bar, ester (5) (1.18 g, 4.00 mmol, 1.0 equiv.) and $H_2PtCl_6.6H_2O$ (21 mg, 0.14 mmol, 1.0 mol. %) were loaded. The tube was transferred into a glovebox and $HSiCl_3$ (0.82 mL, 8.04 mmol, 2.0 equiv.) was added to the solution. The tube was tightly fastened then removed from the glovebox. The resulting solution was stirred at 80° C. for 22 h behind a protecting shield. Purification was achieved by Kugelrohr distillation under high vacuum and provided 1.16 g (67%) of TTTA (6) as a colorless oil; bp=170-180° C. (0.15 Torr); $^1H$ NMR (400 MHz, $CDCl_3$) δ 4.45 (q, J=8.5 Hz, 2H), 2.41 (t, J=7.4 Hz, 2H), 1.72-1.55 (m, 4H), 1.45-1.22 (m, 18H); $^{13}C$ NMR (100 MHz, $CDCl_3$) δ 172.4, 123.3 (q, J=275.8 Hz), 60.3 (q, J=36.4 Hz), 33.9, 32.0, 29.8, 29.7, 29.6, 29.5, 29.4, 29.2, 29.1, 24.9, 24.5, 22.5.

OEG-TTTA Synthesis

Figure 5:
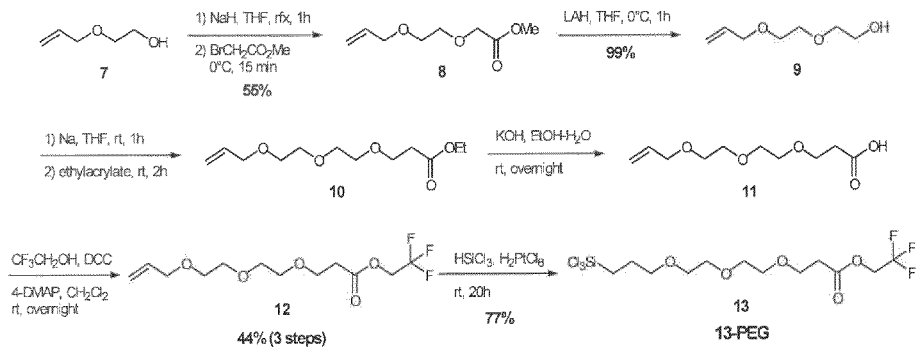
FIG. 5 illustrates Scheme 4, depicting OEG-TTTA synthesis.

FIG. 5 illustrates Scheme 4, depicting OEG-TTTA synthesis. OEG-TTTA (13) was synthesized in six steps from 2-allyloxy-ethanol (7) with a 18% overall yield.

Methyl(2-allyloxy-ethoxy)-acetate (8)

To a stirred solution of 2-allyloxy-ethanol 7 (10.9 mL, 100 mmol, 1.0 equiv.) in THF (200 mL) was carefully added NaH (60%, 4.8 g, 120 mmol, 1.2 equiv.) in small portions at room temperature. The reaction was then refluxed for 1 h (until $H_2$ release ceased) then cooled to 0° C. Methyl bromoacetate (11.4 mL, 120 mmol, 1.2 equiv.) was then added dropwise. After 15 min at 0° C., the reaction was submitted to a EtOAc/$H_2O$ extraction. The combined organic layers were washed with brine, dried over anhydrous $MgSO_4$, filtered then evaporated under reduced pressure. Purification was achieved by Kugelrohr distillation under reduced pressure and provided 9.77 g (55%) of ester (8) as a colorless oil; bp=130-145° C. (water tap vacuum); $^1H$ NMR (400 MHz, $CDCl_3$) δ 5.91 (m, 1H), 5.28 (m, 1H), 4.99 (m, 1H), 4.19 (s, 2H), 4.02 (m, 2H), 3.76 (s, 3H), 3.75 (m, 2H), 3.64 (m, 2H); $^{13}C$ NMR (100 MHz, $CDCl_3$) δ 171.1, 134.8, 117.3, 72.4, 71.2, 69.7, 68.9, 51.9; IR (neat) 1755 cm$^{-1}$; HRMS (ESI, m/z) calcd. for $C_8H_{15}O_4$ (MH$^+$) 175.0964, found 175.0960.

2-(2-allyloxy-ethoxy)-ethanol (9)

To a stirred solution of ester (8) (9.77 g, 55.1 mmol, 1.0 equiv.) in THF (100 mL) was carefully added one portion of LAH (95%, 1.10 g, 27.5 mmol, 0.5 equiv.) at 0° C. After 30 min, another portion of LAH was carefully added and the reaction was stirred for an additional 30 min. The reaction was then carefully quenched with a $Na_2SO_4$-saturated aqueous solution. The resulting white aluminum salts were then filtered off over a short plug of Celite (EtOAc washings) and the filtrate was evaporated under reduced pressure. Purification was achieved by Kugelrohr distillation under reduced pressure and provided 7.99 g (99%) of alcohol (9) as a colorless oil; bp>200° C. (water tap vacuum). Spectroscopic data were consistent with those reported in the literature.[26] $^1H$ NMR (400 MHz, CDCl$_3$) δ 5.92 (m, 1H), 5.28 (m, 1H), 5.19 (m, 1H), 4.04 (m, 2H), 3.73 (m, 2H), 3.68 (m, 2H), 3.62 (m, 4H), 2.36 (brs, 1H).

2,2,2-trifluoroethyl 3-(2-(2-allyloxy-ethoxy)-ethoxy)-propanoate (12)

To a stirred solution of alcohol (9) (8.77 g, 60.0 mmol, 2.2 equiv.) in THF (100 mL) was added freshly hexanes-degreased Na (0.2 g, 8.7 mmol, 0.3 equiv.) in small portions at room temperature. The reaction was then stirred at room temperature for 1 h (until the Na chunks disappeared). A solution of ethyl acrylate (2.97 mL, 27.3 mmol, 1.0 equiv.) in THF (30 mL) was then added dropwise (30 min) through an addition funnel. After 2 h at room temperature, the reaction was quenched with 10 drops of glacial acetic acid then submitted to a CHCl$_3$/H$_2$O extraction. The combined organic layers were dried over anhydrous MgSO$_4$, filtered then evaporated under reduced pressure to provide crude ester (10). The latter was diluted with a 1/1 (v/v) mixture of MeOH (120 mL) and 2.5 M KOH aqueous solution (120 mL). The reaction was vigorously stirred at room temperature overnight then extracted with CHCl$_3$. The aqueous layer was carefully acidified with concentrated (38%) HCl then extracted with CHCl$_3$. The combined organic layers were dried over anhydrous MgSO$_4$, filtered then evaporated under reduced pressure to provide crude acid (11). The latter (4.05 g, 18.6 mmol, 1.0 equiv.) was diluted with CH$_2$Cl$_2$ (120 mL) then DCC (4.25 g, 20.4 mmol, 1.1 equiv.), 2,2,2-trifluoroethanol (1.50 mL, 20.4 mmol, 1.1 equiv.) and 4-DMAP (0.23 g, 1.9 mmol, 0.1 equiv.) were successively added. The reaction was stirred at room temperature overnight then filtered through a short plug of Celite (CH$_2$Cl$_2$ washings). After evaporation of the filtrate under reduced pressure, the final purification was achieved by column chromatography on silica gel (Hexanes/EtOAc gradient) and provided 3.59 g (44%, 3 steps) of ester (12) as a pale yellow oil; $^1$H NMR (400 MHz, CDCl$_3$) δ 5.92 (m, 1H), 5.28 (m, 1H), 5.18 (m, 1H), 4.49 (q, J=8.4 Hz, 2H), 4.03 (m, 2H), 3.79 (t, J=6.4 Hz, 2H), 3.63 (m, 8H), 2.71 (t, J=6.4 Hz, 2H); $^{13}$C NMR (100 MHz, CDCl$_3$) δ 170.2, 134.9, 123.1 (q, J=275.7 Hz), 117.2, 72.4, 70.9, 70.8, 70.7, 69.6, 66.3, 60.5 (q, J=36.5 Hz), 34.8; IR (neat) 1760 cm$^{-1}$; HRMS (ESI, m/z) calcd. for C$_{12}$H$_{20}$O$_5$F$_3$ (MH$^+$) 301.1257, found 301.1258.

2,2,2-trifluoroethyl 3-(2-(2-(3-trichlorosilyl-propyloxy)ethoxy)ethoxy)-propanoate 13 (OEG-TTTA)

In a heavy-walled tube equipped with a magnetic stir bar, ester (12) (1.65 g, 5.50 mmol, 1.0 equiv.) and H$_2$PtCl$_6$.6H$_2$O (28 mg, 0.06 mmol, 1.0 mol. %) were loaded. The tube was transferred into a glovebox and HSiCl$_3$ (1.12 mL, 11.00 mmol, 2.0 equiv.) was added to the solution. The tube was tightly fastened then removed from the glovebox. The resulting solution was stirred at room temperature for 20 h behind a protecting shield. Purification was achieved by Kugelrohr distillation under high vacuum and provided 1.85 g (77%) of OEG-TTTA (13) as a colourless oil; bp=175-185° C. (0.19 Torr); $^1$H NMR (400 MHz, CDCl$_3$) δ 4.47 (q, J=8.4 Hz, 2H), 3.78 (t, J=6.4 Hz, 2H), 3.61 (m, 8H), 3.51 (t, J=6.4 Hz, 2H), 2.70 (t, J=6.4 Hz, 2H), 1.85 (m, 2H), 1.48 (m, 2H); $^{13}$C NMR (100 MHz, CDCl$_3$) δ 170.1, 123.1 (q, J=275.7 Hz), 71.7, 70.8, 70.7, 70.6, 70.3, 66.3, 60.4 (q, J=36.6 Hz), 34.7, 22.7, 21.1.

OEG-TUBTS Synthesis

Figure 6:
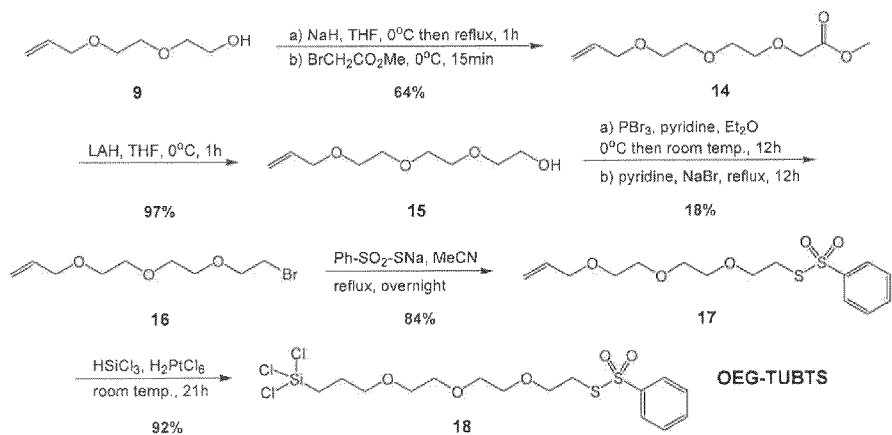
FIG. 6 illustrates Scheme 5, depicting OEG-TUBTS synthesis.

FIG. 6 illustrates Scheme 5, depicting OEG-TUBTS synthesis. OEG-TUBTS (18) was synthesized in five steps from alcohol (9) with a 9% overall yield.

Methyl(2-(2-allyloxy-ethoxy)-ethoxy)-acetate (14)

To a stirred solution of alcohol (9) (4.86 g, 33.2 mmol, 1.0 equiv.) in THF (70 mL) was carefully added NaH (60%, 1.60 g, 40.0 mmol, 1.2 equiv.) in small portions at room temperature. The reaction was then refluxed for 1 h (until H$_2$ release ceased) then cooled to 0° C. Methyl bromoacetate (3.8 mL, 40.1 mmol, 1.2 equiv.) was then added dropwise. After 15 min at 0° C., the reaction was submitted to a EtOAc/H$_2$O extraction. The combined organic phases were washed with brine, dried over anhydrous Na$_2$SO$_4$, filtered then evaporated under reduced pressure. Purification was achieved by distillation under high vacuum and provided 4.68 g (64%) of ester (14) as a colourless oil; bp=130-140 0° C. (0.09 Torr); $^1$H NMR (300 MHz, CDCl$_3$) δ 5.91 (m, 1H), 5.28 (m, 1H), 5.18 (m, 1H), 4.17 (s, 2H), 4.02 (m, 2H), 3.75 (s, 3H), 3.75-3.58 (m, 8H); $^{13}$C NMR (75 MHz, CDCl$_3$) δ 171.0, 134.8, 117.1, 72.3, 71.0, 70.8, 70.7, 69.5, 68.7, 51.8; IR (neat) 1754 cm$^{-1}$; HRMS (ESI, m/z) calcd. for C$_{10}$H$_{19}$O$_5$ (MH$^+$) 219.1236, found 219.1227.

2-(2-(2-allyloxy-ethoxy)-ethoxy)-ethanol (15)

To a stirred solution of ester (14) (4.60 g, 21.1 mmol, 1.0 equiv.) in THF (60 mL) was carefully added one portion of LAH (0.50 g, 12.5 mmol, 0.5 equiv.) at 0° C. After 30 min, another portion of LAH was carefully added and the reaction was stirred for an additional 30 min. The reaction was then carefully quenched with a Na$_2$SO$_4$-saturated aqueous solution. The resulting white aluminum salts were then filtered off over a short plug of Celite (EtOAc washings) and the filtrate was finally evaporated under reduced pressure to afford pure alcohol (15) (no purification required) as a pale yellow oil (3.89 g, 97%). Spectroscopic data were consistent with those reported in the literature:[26a] $^1$H NMR (400 MHz, CDCl$_3$) δ 5.93 (ddt, J=17.2, 10.3, 5.7 Hz, 1H), 5.28 (dq, J=17.2, 1.5 Hz, 1H), 5.19 (dq, J=10.3, 1.5 Hz, 1H), 4.04 (dt, J=5.7, 1.5 Hz, 2H), 3.78-3.58 (m, 12H); $^{13}$C NMR (75 MHz, CDCl$_3$) δ 134.8, 117.3, 72.7, 72.4, 70.8, 70.7, 70.5, 69.5, 61.8.

2-(2-(2-allyloxy-ethoxy)-ethoxy)-1-bromo-ethane (16)

To a stirred solution of alcohol (15) (3.83 g, 20.1 mmol, 1.0 equiv.) and pyridine (0.16 mL, 2.00 mmol, 0.1 equiv.) in Et$_2$O (20 mL) was added dropwise phosphorus tribromide (0.74 mL, 7.60 mmol, 0.36 equiv.) at 0° C. After 30 min, the reaction was allowed to warm to room temperature. As the reaction was not completed after 12 h, pyridine (1.60 mL, 20.0 mmol, 1.0 equiv.) and sodium bromide (4.14 g, 40.2 mmol, 2.0 equiv.) were successively added. After 12 h of reflux, the resulting solution was submitted to a EtOAc/NH$_4$Cl-saturated aqueous solution extraction. The combined organic phases were dried over anhydrous Na$_2$SO$_4$, filtered then evaporated under reduced pressure. Purification was achieved by column chromatography (Hexanes/EtOAc gradient) to afford bromide (16) (0.90 g, 18%) as a yellow oil; $^1$H NMR (300 MHz, CDCl$_3$) δ 5.93 (ddt, J=17.3, 10.5, 5.7 Hz, 1H), 5.28 (dq, J=17.3, 1.5 Hz, 1H), 5.19 (dq, J=10.5, 1.5 Hz, 1H), 4.03 (dt, J=5.7, 1.5 Hz, 2H), 3.82 (t, J=6.3 Hz, 2H), 3.71-3.65 (m, 6H), 3.64-3.59 (m, 2H), 3.48 (t, J=6.3 Hz, 2H); $^{13}$C NMR (75 MHz, CDCl$_3$) δ 134.9, 117.4, 72.5, 71.4, 70.9, 70.8, 70.7, 69.6, 30.5.

S-(2-(2-(2-allyloxy-ethoxy)-ethoxy)-ethyl)benzenethiosulfonate (17)

To a stirred solution of bromide (16) (0.90 g, 3.6 mmol, 1.0 equiv.) in MeCN (18 mL) was added benzenethionosulfonic acid sodium salt (85%, 1.64 g, 7.1 mmol, 2.0 equiv.) at room temperature. The reaction was refluxed overnight then submitted to a EtOAc/brine extraction. The combined organic phases were dried over anhydrous $Na_2SO_4$, filtered then evaporated under reduced pressure. Purification was achieved by column chromatography (Hexanes/EtOAc gradient) to afford benzenethiosulfonate (17) (1.04 g, 84%, >95% purity) as a pale yellow oil. An additional careful column chromatography afforded pure (17) as a pale yellow oil: $^1$H NMR (300 MHz, $CDCl_3$) δ 7.95 (m, 2H), 7.65 (m, 1H), 7.56 (m, 2H), 5.91 (m, 1H), 5.29 (m, 1H), 5.19 (m, 1H), 4.01 (m, 2H), 3.74-3.56 (m, 10H), 3.20 (t, J=6.3 Hz, 2H); $^{13}$C NMR (75 MHz, $CDCl_3$) δ 145.0, 134.9, 133.9, 129.5, 127.2, 117.3, 72.4, 70.8, 70.7, 70.6, 69.6, 69.2, 35.9; IR (neat) 3068, 1647, 1324, 1142 cm$^{-1}$; HRMS (ESI, m/z) calcd. for $C_{15}H_{23}S_2O_5$ (MH$^+$) 347.0971, found 347.0981.

S-(2-(2-(2-(3-trichlorosilyl-propyloxy)-ethoxy)-ethoxy)-ethyl)benzenethiosulfonate (18) (OEG-TUBTS)

In a heavy-walled tube equipped with a magnetic stirring bar, benzenethiosulfonate (17) (347 mg, 1.00 mmol, 1.0 equiv.) and $H_2PtCl_6·6H_2O$ (5.2 mg, 0.010 mmol, 1.0 mol. %) were loaded. The tube was transferred into a glovebox and $HSiCl_3$ (0.30 mL, 2.94 mmol, 3.0 equiv.) was added to the solution. The tube was tightly fastened then removed from the glovebox. The resulting solution was stirred at room temperature for 21 hours behind a protecting shield. $HSiCl_3$ excess was then removed under high vacuum to afford OEG-TUBTS (18) as a viscous yellow-orange cloudy oil (444 mg, 92%): $^1$H NMR (300 MHz, $CDCl_3$) δ 7.94 (m, 1H), 7.62 (m, 1H), 7.58 (m, 1H), 7.46 (m, 1H), 7.32 (m, 1H), 3.85-3.55 (m, 16H), 3.20 (t, J=6.2 Hz, 1H), 2.80 (t, J=6.2 Hz, 1H).

7-OEG Synthesis

Figure 7:
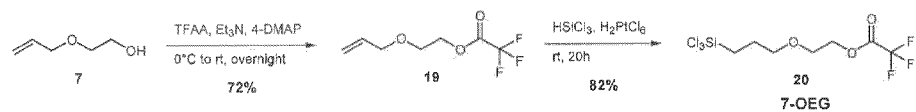
FIG. 7 illustrates Scheme 6, depicting 7-OEG synthesis.

FIG. 7 illustrates Scheme 6, depicting 7-OEG synthesis. 7-OEG (20) was synthesized in two steps from 2-allyloxy-ethanol 7 with a 59% overall yield.

2-allyloxy-ethyl trifluoroacetate (19)

To a stirred solution of 2-allyloxy-ethanol (7) (4.36 mL, 40.0 mmol, 1.0 equiv.), $Et_3N$ (11.2 mL, 80.0 mmol, 2.0 equiv.) and 4-DMAP (0.49 g, 4.0 mmol, 0.1 equiv.) in $CH_2Cl_2$ (80 mL) was added dropwise trifluoroacetic anhydride (6.74 mL, 48.0 mmol, 1.2 equiv.) at 0° C. After addition, the reaction was allowed to warm to room temperature then stirred overnight. The reaction was then submitted to a $CH_2Cl_2$/$NH_4Cl$-saturated aqueous solution extraction. The combined organic layers were dried over anhydrous $MgSO_4$, filtered then evaporated under reduced pressure. Purification was achieved by distillation under reduced pressure and provided 5.76 g (72%) of ester (19) as a colourless oil: bp=72-74° C. (water tap vacuum); $^1$H NMR (300 MHz, $CDCl_3$) δ 5.88 (m, 1H), 5.29 (m, 1H), 5.21 (m, 1H), 4.52 (t, J=4.8 Hz, 2H), 4.03 (m, 2H), 3.76 (t, J=4.8 Hz, 2H); $^{13}$C NMR (75 MHz, $CDCl_3$) δ 157.7 (q, J=42.1 Hz), 134.2, 117.8, 114.7 (q, J=283.9 Hz), 72.4, 67.2, 67.0.

2-(3-trichlorosilyl-propyloxy)-ethyl trifluoroacetate (7-OEG) (20)

In a heavy-walled tube equipped with a magnetic stir bar, ester (19) (3.97 g, 20.0 mmol, 1.0 equiv.) and $H_2PtCl_6·6H_2O$ (104 mg, 0.20 mmol, 1.0 mol. %) were loaded. The tube was transferred into a glovebox and $HSiCl_3$ (4.10 mL, 40.2 mmol, 2.0 equiv.) was added to the solution. The tube was tightly fastened then removed from the glovebox. The resulting solution was stirred at room temperature for 20 h behind a protecting shield. Purification was achieved by Kugelrohr distillation under high vacuum and provided 5.46 g (82%) of 7-OEG (20) as a colourless oil; bp=115-120° C. (0.09 Torr); $^1$H NMR (400 MHz, $CDCl_3$) δ 4.52 (m, 2H), 3.76 (m, 2H), 3.56 (t, J=6.2 Hz, 2H), 1.85 (m, 2H), 1.48 (m, 2H); $^{13}$C NMR (100 MHz, $CDCl_3$) δ 157.7 (q, J=42.3 Hz), 114.7 (q, J=284.1 Hz), 71.8, 67.9, 67.0, 22.8, 21.0.

Biotinthiol Synthesis

Figure 8:
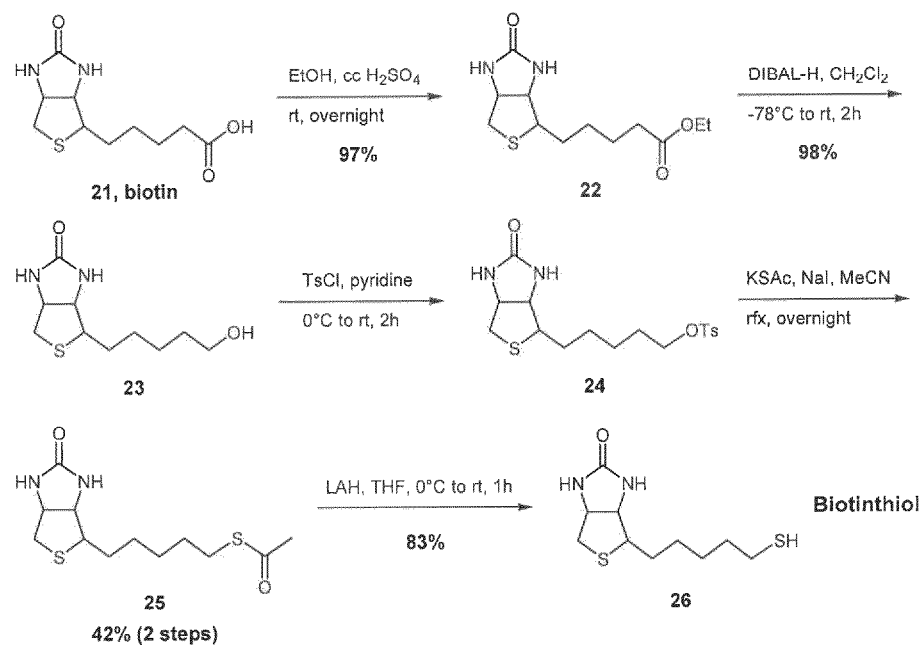
FIG. 8 illustrates Scheme 7, depicting biotinthiol synthesis.

FIG. 8 illustrates Scheme 7, depicting biotinthiol synthesis. Biotinthiol (26) was synthesized in five steps from biotin (21) with a 33% overall yield.

Biotin Methyl Ester (22).[27]

To a stirred solution of biotin (21) (900 mg, 3.65 mmol, 1.0 equiv.) in absolute EtOH (30 mL) were added few drops of concentrated $H_2SO_4$ at room temperature. After stirring at room temperature overnight, the reaction was submitted to a $CH_2Cl_2$/$Na_2CO_3$-aqueous solution extraction. The combined organic layers were dried over anhydrous $Na_2SO_4$, filtered then evaporated under reduced pressure to provide 961 mg (97%) of ester 22 as a white solid. Spectroscopic data were consistent with those reported in the literature.[27] $^1$H NMR (400 MHz, $CDCl_3$) δ 5.55 (brs, 1H), 5.17 (brs, 1H), 4.54 (m, 1H), 4.34 (m, 1H), 4.15 (q, J=7.2 Hz, 2H), 3.18 (m, 1H), 2.93 (dd, J=12.8, 4.8 Hz, 1H), 2.75 (d, J=12.8 Hz, 1H), 2.36 (t, J=7.6 Hz, 2H), 1.69 (m, 4H), 1.45 (m, 2H), 1.24 (t, J=7.2 Hz, 3H).

Biotinol 23.[27]

To a stirred solution of biotin methyl ester (22) (961 mg, 3.53 mmol, 1.0 equiv.) in $CH_2Cl_2$ (10 mL) was added dropwise DIBAL-H (1.0 M in hexanes, 12.4 mL, 12.4 mmol, 3.5 equiv.) at −78° C. After addition, the reaction was allowed to warm to room temperature then stirred for 2 h. The reaction was then carefully quenched, at −78° C., by dropwise addition of MeOH then $H_2O$. After evaporation of the solvents under reduced pressure, the purification was achieved by Soxhlett extraction (EtOH) and provided 796 mg (98%) of biotinol (23) as a white solid; $^1$H NMR (400 MHz, $CD_3OD$) δ 4.49 (dd, J=7.8, 4.8 Hz, 1H), 4.30 (dd, J=7.8, 4.8 Hz, 1H), 3.55 (t, J=6.6 Hz, 2H), 3.21 (m, 1H), 2.93 (dd, J=12.6, 4.8 Hz, 1H), 2.71 (d, J=12.6 Hz, 1H), 2.16 (s, 1H), 1.74 (m, 1H), 1.57 (m, 3H), 1.45 (m, 4H).

Biotin Tosylate[28] (24) and Biotin Thiocetate (25).

To a stirred solution of biotinol (23) (796 mg, 3.46 mmol, 1.0 equiv.) in pyridine (20 mL) was added tosyl chloride (1.75 g, 9.09 mmol, 2.6 equiv.) at 0° C. After addition, the reaction was allowed to warm to room temperature then stirred for 2 h. The reaction was then submitted to a $CH_2Cl_2$/1 M $H_2SO_4$ aqueous solution extraction. The combined organic layers were dried over anhydrous $Na_2SO_4$, filtered then evaporated under reduced pressure. The residue was rapidly purified by column chromatography on silica gel (EtOAc/MeOH gradient) to provide 697 mg of an off-white solid. The latter was immediately dissolved in anhydrous MeCN (30 mL) then anhydrous NaI (2.65 g, 17.7 mmol) and KSAc (2.06 g, 17.7 mmol) were successively added at room temperature. The reaction was refluxed overnight then submitted to a $CH_2Cl_2$/$H_2O$ extraction. The combined organic layers were washed with brine, dried over anhydrous $Na_2SO_4$, filtered then evaporated under reduced pressure. Purification was achieved by column chromatography on silica gel ($CH_2Cl_2$/MeOH gradient) and provided 417 mg (42%, 2 steps) of biotin thioacetate (25) as a beige solid. Spectroscopic data were consistent with those reported in the literature.[29] $^1$H NMR (400 MHz, $CDCl_3$) δ 5.22 (brs, 1H), 4.86 (brs, 1H), 4.55 (m, 1H), 4.34 (m, 1H), 3.17 (m, 1H), 2.94 (dd, J=12.8, 5.2 Hz, 1H), 2.87 (t, J=7.4 Hz, 2H), 2.76 (d, J=12.8 Hz, 1H), 2.36 (s, 3H), 1.64-1.57 (m, 4H), 1.42 (m, 4H).

Biotinthiol (26).[29]

To a stirred solution of biotin thioacetate (25) (410 mg, 1.42 mmol, 1.0 equiv.) in THF (40 mL) was added LAH (95%, 454 mg, 11.36 mmol, 8.0 equiv.) in small portions at 0° C. After addition, the reaction was allowed to warm to room temperature then stirred for 1 h. The reaction was diluted with EtOAc then carefully quenched with a 1 M HCl aqueous solution. The resulting aqueous layer was extracted with EtOAc. The combined organic layers were washed with brine, dried over anhydrous $Na_2SO_4$, filtered then evaporated under reduced pressure. Purification was achieved by column chromatography on silica gel (EtOAc/MeOH gradient) and provided 291 mg (83%) of biotinthiol (26) as a white solid. Spectroscopic data were consistent with those reported in the literature.[29] $^1$H NMR (300 MHz, $CDCl_3$) δ 5.00 (brs, 1H), 4.84 (brs, 1H), 4.55 (m, 1H), 4.35 (m, 1H), 3.20 (m, 1H), 2.95 (dd, J=12.8, 5.2 Hz, 1H), 2.76 (d, J=12.8 Hz, 1H), 2.56 (q, J=7.3 Hz, 2H), 1.76-1.59 (m, 4H), 1.53-1.40 (m, 4H), 1.37 (t, J=7.3 Hz, 1H).

Surface Analyses: Contact Angle Measurement (CAM)

Contact angle measurements (static) were performed in the Department of Chemistry, University of Toronto, Toronto, Canada. Surfaces were analyzed with the KSV contact angle measurement instrument (KSV Instruments Ltd., Linthicum Heights, Md., USA) and ultrapure water as the test liquid. Contact angle values were generated using the CAM101 software.

Surface Analyses: X-Ray Photoelectron Spectroscopy (XPS)

Angle-resolved XPS analysis was performed with a Theta probe ThermoFisher Scientific Instrument (East Grinstead, UK) located at Surface Interface Ontario, University of Toronto, Toronto, ON, Canada. The samples were analyzed with monochromated Al Kα X-rays (elliptical spots of 400 μm along the long axis), with take-off angles of 72.5° and 27.5° relative to the surface. The binding energy scale was calibrated to the main C1s signal at 285 eV. Peak fitting and data analysis were performed using Avantage software provided with the instrument (Table 2).

TABLE 2

Angle-resolved XPS analysis

| Surface | XPS angle | % C1s 285 eV | % F1s 685 eV | % O1s 531 eV | % Si2p 100 eV | % S2p 163 eV |
|---|---|---|---|---|---|---|
| Cleaned quartz disc | 72.5° | 20.1[a] | 0.0 | 52.0 | 27.9 | 0.0 |
|  | 27.5° | 6.5[a] | 0.0 | 56.4 | 37.1 | 0.0 |
| TTTA/OTS SAM | 72.5° | 26.6 | 2.1 | 48.0 | 23.4 | 0.0 |
|  | 27.5° | 9.0 | 0.9 | 55.6 | 34.5 | 0.0 |
| OEG-TTTA/7-OEG SAM | 72.5° | 19.8 | 3.2 | 54.6 | 22.4 | 0.0 |
|  | 27.5° | 6.7 | 1.2 | 56.9 | 35.2 | 0.0 |
| OEG-TUBTS/7-OEG SAM | 72.5° | 31.4 | 6.5 | 44.2 | 16.5 | 1.4 |
|  | 27.5° | 25.7 | 5.8 | 45.7 | 21.3 | 1.5 |

Angle-resolved XPS analysis (72.5° (surface) and 27.5° (bulk)) for cleaned disc as well as TTTA/OTS, OEG-TTTA/7-OEG and OEG-TUBTS/7-OEG mixed SAMs.
[a]This signal is due to unavoidable surface contamination by adventitious carbon.

Angle-resolved XPS data (along with CAMs in Table 1) were used to determine whether the linker and diluent molecules had deposited from solution onto the quartz slides. Atomic percentages for characteristic elements of the linker/diluent molecules (fluorine and sulfur) along with those for elements (mainly) present in quartz (silicon and oxygen) were calculated and compared before (clean quartz crystal) and after linker/diluent deposition. As expected, clean quartz crystals only showed Si and O as well as unavoidable adventitious carbon. Upon deposition of TTTA/OTS molecules, XPS data were as expected: F signal appeared (and was higher at the surface) and the signals of the underlying buried O and Si decreased. The same was true for the OEG-TTTA/7-OEG system except for the O surface signal, which slightly increased because both OEG-TTTA and 7-OEG molecules possess a non-neglectable amount of O that was reflected in the total amount of O. As expected as well for the OEG-TUBTS/7-OEG system, F and S signals appeared (showing that both molecules deposited) and the signals of the underlying buried O and Si decreased.

Example 2

Modification of Commonly Used Biomedical Polycarbonate Using Short Chain Silane Adlayers for Removal of Blood Fouling The following example describes the process of fouling reduction from polycarbonate surface using adlayer coating. The coating is self-assembled onto plasma-activated polycarbonate surface from previously unreported molecule. Using blood with platelets labelled with fluorescence active molecule, an inverted fluorescence microscope equipped with a camera is used for measuring real time blood deposition onto surfaces. Coated surfaces display lower density of attached platelets compared to bare surfaces with no modification. The work constitutes the first time an ethylene glycol SAM is attached to polycarbonate for antifouling properties. For other polymers, i.e. polyurethane, it is the first time an organosilane SAM is attached.

Methodology

The following includes detailed protocols for polymer surface cleaning with activation, SAM deposition, SAM activation and antifouling analysis. Polycarbonate (PC) sheets (1/16 inch-thick) were purchased from SABIC polymer shapes (New Orleans, La.). POP, PVC and PUR (1/16 inch-thick) were purchased from Macmaster Carr (Aurora, Ohio). PET plastics were cut from Nalgene water bottles ordered from Sigma-Aldrich. Hexadecane, ethanol (95%), 3,3'-Dihexyloxacarbocyanine Iodide ($DiOC_6$) were purchased from Sigma-Aldrich and used as is. Milli-Q water was used at 18.1 Mohm. Heptane, toluene, sodium dodecyl sulfate (SDS) and hexanes solutions were purchased from Caledon Laboratories. SDS was dissolved in milli-Q water in proportions of 1 g/100 ml. The rectangular perfusion chamber was purchased from Glycotech (Gaithersburg, Md.). MEG-TFA and MEG-OH films were prepared following a previously described procedure.[32] All steps of film formation were thoroughly characterized and tested for completeness.

FIG. 9 illustrates a generalized surface modification for application to polymers having or capable of being converted to hydroxyl groups. Step 1) involves plasma activation, step 2) involves deposition of MEG-TFA onto the surface, and step 3) involves conversion of MEG-TFA to MEG-OH. Each step is elaborated upon below.

Surface Activation.

All samples undergo the same washing step sequence but require different solvents depending on their compatibility properties. All plastics undergo a wash in warm tap water and distilled water before any experimental setup. After the samples are placed in 1% SDS solution and put on a rotating plate for 5 minutes, the samples are finally washed twice with the SDS solution. After the wash, the samples are washed with tap and DI water as previously stated. The samples are then placed into solvent 2 and washed following the same procedure used with SDS, using the exemplary solvents outlined in Table 3. Other polymers will require other solvents depending on compatibility.

TABLE 3

Compatible Solvent 2 for Different Polymers

| Polymer | Solvent 2 |
|---|---|
| PET | Methanol |
| PC | Ethanol (95%) |
| POP | Acetone |
| PVC | Ethanol (95%) |
| PUR | Ethanol (95%) |

After the wash, the samples are dried with $N_2$ gas and placed into a plasma cleaner (Harrick Plasma—13.56 MHz frequency, 30 W power, air plasma). The time depends on the polymer, as outlined in Table 4.

TABLE 4

Plasma Cleaning Times for Different Polymers

| Polymer | Time required (sec) |
|---|---|
| PET | 300 |
| PC | 1200 |
| POP | 2100 |
| PVC | 60 |
| PUR | 45 |

Other polymer-based materials could be optimized with the same general procedure. After plasma cleaning, the samples are placed into the humidity chamber (80% humidity, room temperature) overnight.

Silanization Procedure.

The samples were taken out from the humidity chamber and placed into pre-silanized glassware. Under nitrogen atmosphere the samples were placed into 1 µl/1 ml solutions of linker/solvent 3 solution. Table 5 outlines exemplary choices for solvent 3.

TABLE 5

Compatible Solvent 3 for Different Polymers

| Polymer | Solvent 3 |
|---|---|
| PET | Toluene |
| PC | Hexanes |
| POP | Hexanes |
| PVC | Heptane |
| PUR | Heptane |

Glassware was capped and placed on a spinner for 1 hour. Samples were then rinsed three times with solvent 3 and sonicated in the same solvent. This procedure was repeated with ethanol (95%). Samples were finally dried with $N_2$ then placed into solvent 4 (see Table 6) and left on the spinning plate overnight.

TABLE 6

Compatible Solvent 4 for Different Polymers

| Polymer | Solvent 4 |
|---|---|
| PET | Methanol + DI water (50:50) |
| PC | Ethanol + DI water (50:50) |
| POP | Ethanol + DI water (50:50) |

TABLE 6-continued

Compatible Solvent 4 for Different Polymers

| Polymer | Solvent 4 |
|---|---|
| PVC | DI Water |
| PUR | DI Water |

Samples were removed from the glassware and rinsed with solvent 4 three times. Samples were finally dried with $N_2$ gas and used for different analysis.

Surface Analysis for Linker Deposition

CAG.

Contact angles were measured on a KSV contact angle measurement instrument (KSV Instruments Ltd.). The analysis of the contact angle was executed on CAM101 software. The experiments involved three test liquids: milli-Q water, hexadecane and ethylene glycol. For the calculations of surface energy, the Good & Van Oss theory[41] was used.

ATR-IR.

ATR-IR was done on a vertex 70 spectrometer using a contact angle of 45 degrees. Opus 6.5™ software was used for data analysis. Analysis was performed for all surfaces in triplicate then averaged.

XPS.

XPS analysis was performed with a theta probe Thermo Fisher Scientific instrument at a takeoff angle of 90°, under low resolution. Samples were analyzed using monochromated Al Kα x-rays. Analyzed elements included carbon, oxygen, fluorine, and silicon. Avantage™ software was used to analyze the data.

Blood Analysis.

The main analyses were done on polycarbonate surfaces with unmodified and MEG-OH-coated surfaces. For positive control, an unmodified surface was coated with collagen.

Blood samples were received from human donors. The blood was labelled with $DIOC_6$ for 10 minutes at 37° C. The blood was perfused using a rectangular perfusion chamber under controlled flow rate using a syringe pump. Surfaces were analyzed using Zeiss Axiovert™ 135 inverted fluorescence microscopy with images taken using a DP70 digital camera (Olympus). Data was analyzed using Slidebook™ and ImageJ™ softwares. Blood was flown for about 7 minutes over the samples.

Results and Discussion

XPS Analysis.

XPS analysis was performed on three types of PC samples: plasma-activated, MEG-TFA- and MEG-OH-coated.

Figure 10:
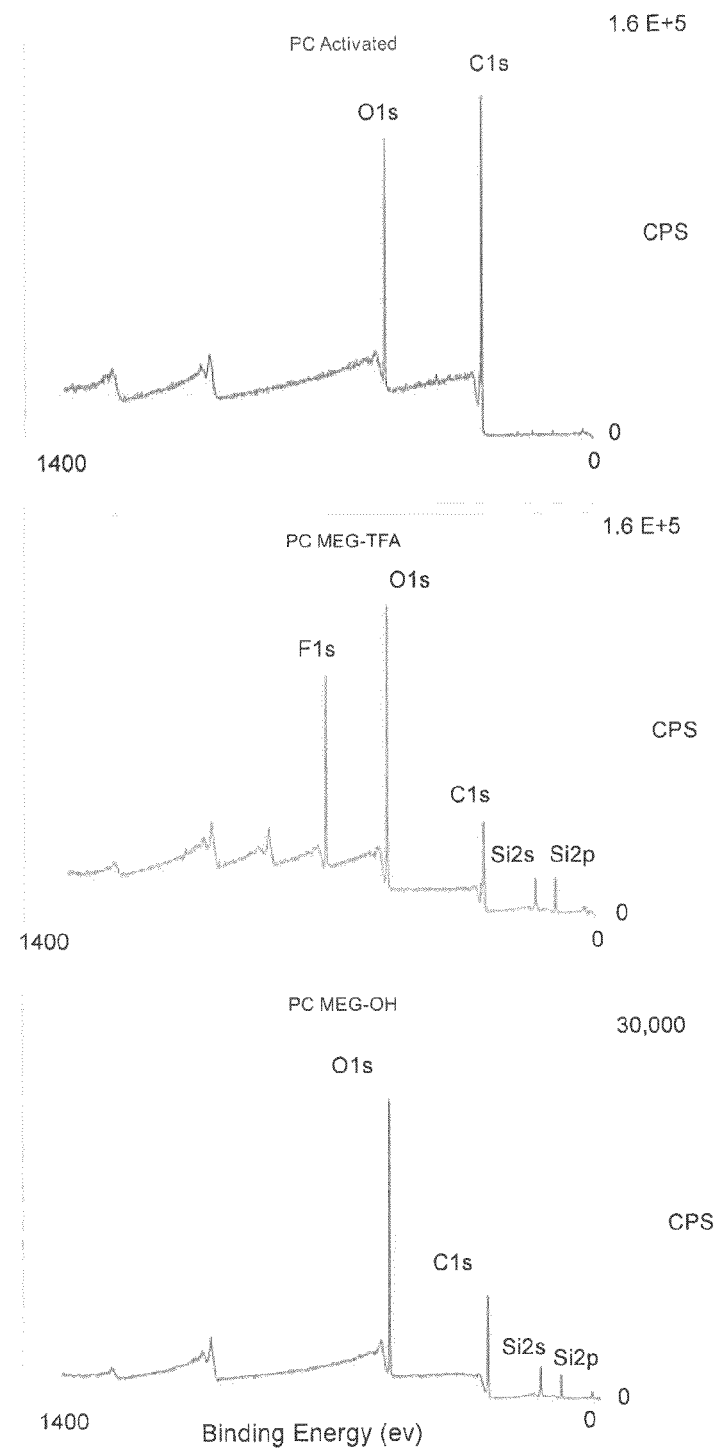
FIG. 10 shows the results of modifying a polycarbonate surface using XPS elemental analysis upon a) plasma activation, b) MEG-TFA deposition, and c) conversion of MEG-TFA to MEG-OH.

FIG. 10 shows the results of modifying the polycarbonate surface using XPS elemental analysis upon a) plasma activation, b) MEG-TFA deposition, and c) conversion of MEG-TFA to MEG-OH. Analysis was done to check for elemental composition. Samples were analyzed for composition of four atoms (C, O, Si, and F) to identify the surface elemental composition and bond nature. Elemental composition can give an indication for the presence of thin films on the surface when the peak intensity is significantly higher in coated surfaces compared to the uncoated surfaces. Analysis of individual peak shifts can also give information on the nature of the bonds involved between polymer substrate and SAM.

Figure 11:
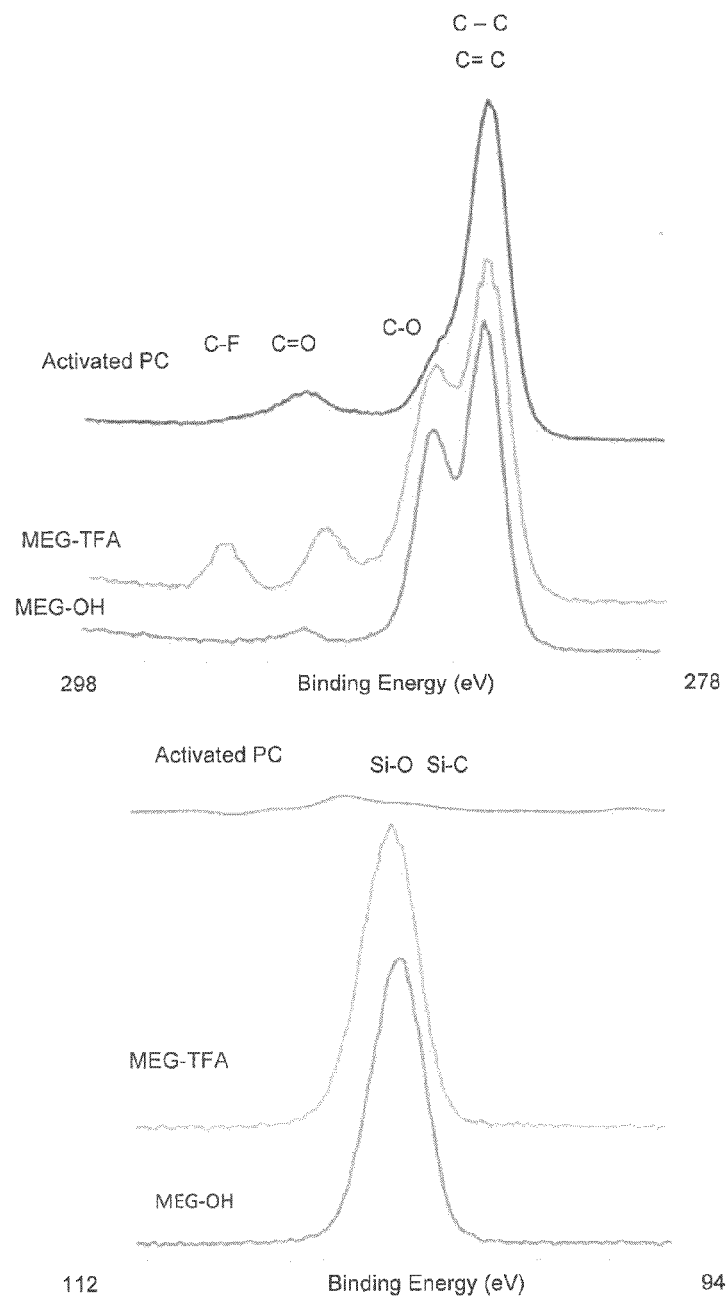
FIG. 11 shows XPS peak analysis for the a) carbon and b) silicon elements at different stages of polycarbonate modification.

FIG. 11 shows XPS peak analysis for the a) carbon and b) silicon elements at different stages of polycarbonate modification.

For film identification using XPS, several peaks were selected, including $C_{1s}$ at 285, $O_{1s}$ at 532 eV, $Si_{2p}$ at 100 eV, $Si_{2s}$ at 158 eV, and $F_{1s}$ at 688 eV.[5]

When analyzing MEG-TFA coated surfaces, new elements with significant increases were observed notably $F_{1s}$ and Si (2p & 2s) peaks at 688 and 102 & 158 eV, respectively. The MEG-TFA sample had increased in silicon composition from 0 to 13%, as outlined in Table 7. The increased peak is due to the presence of an anchoring silicon-based film. Fluorine content increased from 0 to 6% due to the TFA protective group. Both fluorine and silicon are indicators of the film on the surface neither being previously observed in the activated bare samples. Other noticeable changes are the decrease in carbon and increase in oxygen concentrations from 76 to 45% and 22 to 35%, respectively (see Table 7). Other elements are below the limit of detection for this sample at <1%. When observing the carbon peak, several shifts can be seen. The main peak, which is located at 285 eV, corresponds to C—C and C=C. Due to low resolution, these two peaks could not be fully differentiated. Another peak located at 291 eV corresponds to the C=O ketone group. A small peak is present at 287 eV, which corresponds to C—O due to the formation of OH groups on the surface from plasma activation. The oxygen peak could not be resolved due to low resolution. The composition is as expected with each PC unit having mostly carbon atoms and oxygen in the monomeric building blocks. The carbon content is higher in the bulk of PC compared to the surface content (film) where the carbon percentage is significantly lower.

TABLE 7

PC Surface Properties

| Peak | Plasma activation (At. %) | MEG-TFA (At. %) | MEG-OH (At. %) |
|---|---|---|---|
| $C_{1s}$ | 76.25 | 44.73 | 47.50 |
| $O_{1s}$ | 22.81 | 36.76 | 38.94 |
| $F_{1s}$ | 0.01 | 5.92 | 0.1 |
| $Si_{2p}$ | 0.93 | 12.58 | 13.45 |

The bonds corresponding to MEG-TFA have a few additional types of bond compared to the activated bare surface. One of the new carbon bond seen in this case is a peak at 294 eV corresponding to the C—F bonding located at the TFA protective group. The bonds at 287 and 291 eV have significantly increased in intensity in MEG-TFA compared to activated bare surface (see FIG. 11). The peak at 287 eV corresponds to the C—O bond that is likely the backbone C—O—C and possibly C—O—Si bond connecting the film to the surface. The increase at 291 eV corresponds to the C=O bond that is part of the TFA group of the film. With respect to silicon, the signal at 102 eV can be attributed to $CSiO_3$ group.[34] Also, other sources propose this peak to be an indication for increased presence of C—Si—O film (101.4-101.6 range).[35,36] The group is attributed to the cross-linking and anchor in the film.

When treated with ethanol/water solution, MEG-TFA is converted to MEG-OH. The most significant change was observed for the fluorine content, which decreased from 6 to 0%. Comparatively, other elements had no significant changes. Observations are consistent with the removal of TFA protective group from the film. When analyzing the peaks for carbon, it was noted a significant decline in C=O bonding peak at 291 eV and complete removal of the C—F peak at 294 eV (see FIG. 11), which corresponds to bonds from the TFA group. Data show successful conversion of MEG-TFA to MEG-OH ones, without etching of the residual film, under the aqueous conditions. Similar results have been reported with quartz.[32]

ATR-IR Analysis.

Figure 13:
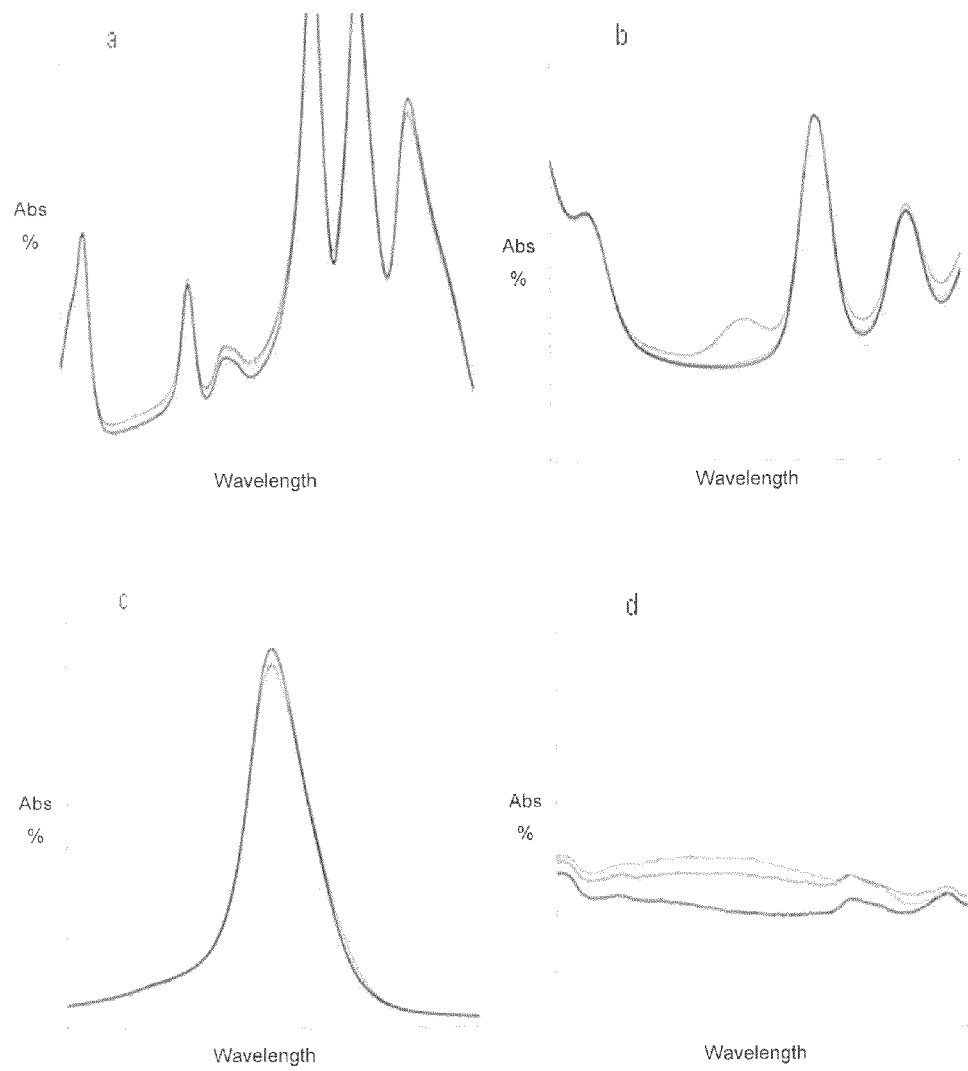
FIG. 13 shows various portions of ATR-infrared spectra obtained upon surface modifications of polycarbonate.
Figure 14:
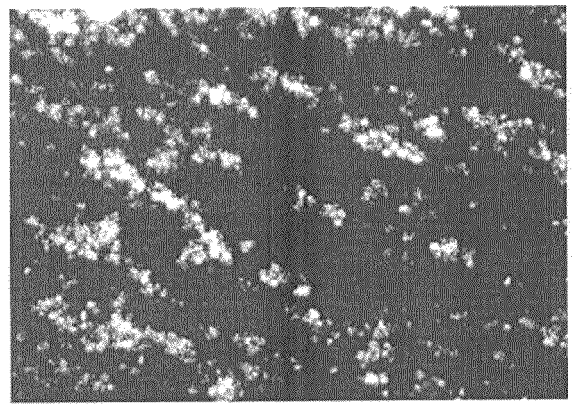
FIG. 14 depicts fluorescence analysis of platelet adhesion on collagen-coated polycarbonate surface. As depicted here, bright areas represent green areas of fluorescence indicative of adhesion of platelets. Areas of aggregates are considered as thrombus, while individual dots are not counted in analysis.
Figure 15:
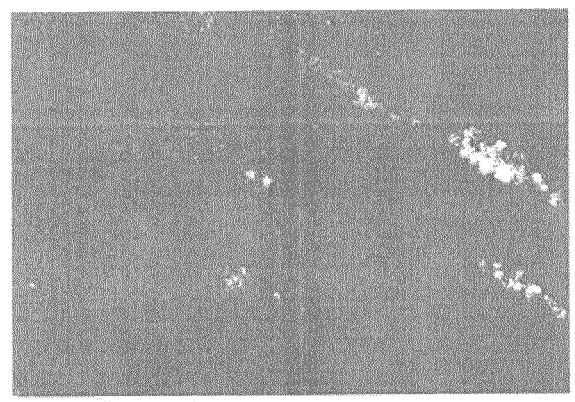
FIG. 15 depicts fluorescence analysis of platelet adhesion on an unmodified polycarbonate surface, showing less platelet adhesion relative to the collagen-coated surface of FIG. 14.
Figure 16:
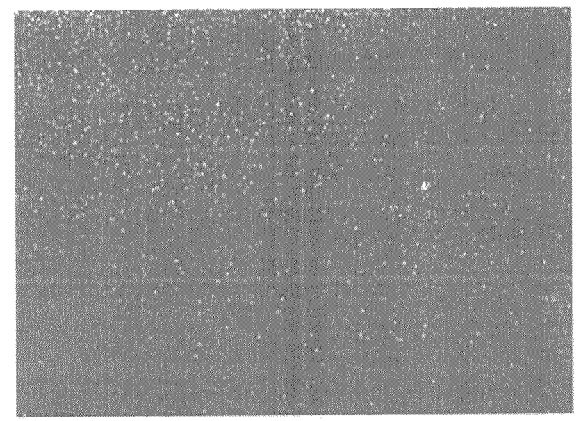
FIG. 16 depicts fluorescence analysis of platelet adhesion on a MEG-OH-coated polycarbonate surface, showing less platelet adhesion relative to both the collagen-coated surface of FIG. 14 and the unmodified surface of FIG. 15.

The analysis was executed in triplicates on three types of PC surfaces: plasma-activated, MEG-TFA and MEG-OH. For comparison purposes, data from all PC surfaces is overlapped to show peak changes. Several areas show differences between the plasma activated and MEG-TFA/MEG-OH-coated surfaces, with major peaks at: 1020-1080, 1100, 1348, 1768, and 3200-3600 cm$^{-1}$ (see FIG. 13). Due to high overlap from different bonds, some of the peaks corresponding to silicon could not be observed thus are not included in the analysis.

The broad peaks observed at 1020-1080 cm$^{-1}$ do not form independent peak but are consistently higher on MEG-TFA and MEG-OH-coated PC samples. The range of this frequency has been previously reported to correspond to Si—O—Si asymmetric stretching, which has been reported in many film and gel structures previously.[38,39,40] In the current layer, the structure represents the cross-linking between the molecules forming the film.

Another peak at 1100 cm$^{-1}$ is observed in both MEG-TFA and MEG-OH films. The peak is located at the Si—O vibrational range and has been previously assigned to the formation of Si—O—C asymmetric stretch in gels and surface coatings.[37] The structure corresponds to the anchor group linking to the PC surface. The peak corresponds to likely formed covalent bond on the surface of PC based on trichlorosilane SAM interaction with hydroxylated surfaces.[40] Another peak that is a good indicator of a film is located at 1348 cm$^{-1}$ corresponding to the C—F stretch. The peak is only present in the surface that has been coated with MEG-TFA. The peak disappears when the coating transforms into MEG-OH and as a result is a good indicator of TFA group removal from the sample.

The peak at 1768 cm$^{-1}$ corresponds to the C=O stretch bond and decreased with the formation of MEG-OH from MEG-TFA coating.

The broad peak located at 3200-3600 cm$^{-1}$ is at high intensity for MEG-TFA and higher intensity for MEG-OH. The peak has been previously reported for O—H vibration. In the case of this surface, it is likely that there is formation of $H_2O$ hydrogen bonds linking with the ether group and distal OH groups of the film. There is no formation of this kind of H-bonding on the activated (bare) surface with —OH groups. Thus, it is likely that water is trapped within the film forming hydrogen bonds with the oxygen atoms of the ethylene glycol moieties. The following results have not been previously attributed to PC surfaces coated with ethylene glycol based films. Such hydration feature may lead to the formation of an interfacial water barrier from which antifouling properties may emanate.

Surface Energy Analysis.

Using the Good & Van Oss theory,[41] surface energy was calculated for four stages of PC coating: unmodified, plasma activated, MEG-TFA and MEG-OH, as shown in Table 8. Other polymers have shown the same data pattern. This analysis could serve as a preliminary indicator of surface modification by different layers. The analysis of unmodified surface determined values of 25.1 mJ/m$^2$, which are typical for non-polar polymers. The value for plasma-activated surfaces was calculated to be 47.3 mJ/m$^2$. The increase in surface energy can be attributed to a surface with higher wettability and more polar character, air plasma activation on PC inducing the formation of polar groups at the surface (COOH, C=O, —OH).[39] Such increase in surface energy is favourable for antifouling properties.

TABLE 8

Surface Energy at Different Stages of PC modification

| Surface type | Surface energy (mJ/m$^2$) |
|---|---|
| Unmodified | 25.1 |
| Activated | 47.3 |
| MEG-TFA | 24.6 |
| MEG-OH | 39.8 |

Groups favourable for antifouling return to their original surface energy after several days of exposure.[39] When treated with MEG-TFA, surface energy decreased to the value of 24.6 mJ/m$^2$. These results correspond to a decreased polar character, which occurs with the presence of C—F bonds on the surface from the TFA protecting group. After conversion to MEG-OH, the surface energy increased to 39.8 mJ/m$^2$. This increase corresponds to higher wettability due to the presence of hydroxyl groups from the film. High surface energy is favourable for low fouling thus the surface is likely to be good for fouling reduction. Due to their high surface energy, the MEG-OH surfaces would likely be beneficial for use in medical equipment to combat fouling.

Blood Analysis (Only PC was Analyzed).

Using imageJ software, platelet adhesion to the different PC surface stages was quantified. When analyzing PC samples for surface coverage, unmodified samples was 3-7% from the total surface. In stark contrast, the surface coverage for coated surfaces was only 0.06-0.1%. These results show a significant decrease in surface coverage on coated surfaces compared to unmodified or collagen-based surfaces. Decreased coverage shows decreased adhesion of platelets and other blood cells from the blood to the surface. The result likely produces less damaged or modified cells in the blood due to interaction with the surface. When those cells are attached to the surface, it activates the intrinsic and extrinsic pathways of blood clotting. The cascades result in the formation of a netting of fibrin and accumulate more cells to the surface.[31] With lower coverage, it is seen that there is going to be significantly reduced risk of the occurrence of the cascade in medical devices undergoing contact with blood.

Conclusion

The method of the current example could be used to modify different types of current biomedical polymers. Several polymers have been tested including PET, PC, POP, PVC and PUR. The procedure is possible for other currently used polymers that could be activated using plasma. The films were confirmed using surface energy by changes that correspond to the head groups of the film indicating significant changes in surface wettability properties depending on the head group. Analysis using ATR-IR confirmed the ability of the films to form cross-linking Si—O—Si bonds and Si—O—C bonds with the surface. Film elemental and covalent bond composition could be confirmed with XPS. Film properties have a high potential of properties that reduce fouling. Analyses of the film ability to reduce fouling have proved successful in eliminating the majority of cell adhesion onto the surfaces. Overall, all the indicators have positively indicated that the surface has a film deposited. It is also able to function by reducing the majority of the fouling on the polymer when in contact with blood.

When analyzing POP unmodified surface, the oxygen composition of the surface was at 2% compared to the activated surface (12%), as outlined in Table 9. The higher content of oxygen on the activated surface is a result of air oxidation on POP surfaces.[33] Thus, formation of hydroxyl groups on the surface of polymers is confirmed. Results show a clear increase of oxygen content on the surface supporting that air plasma oxidation does occur on the POP surface.

Figure 12:
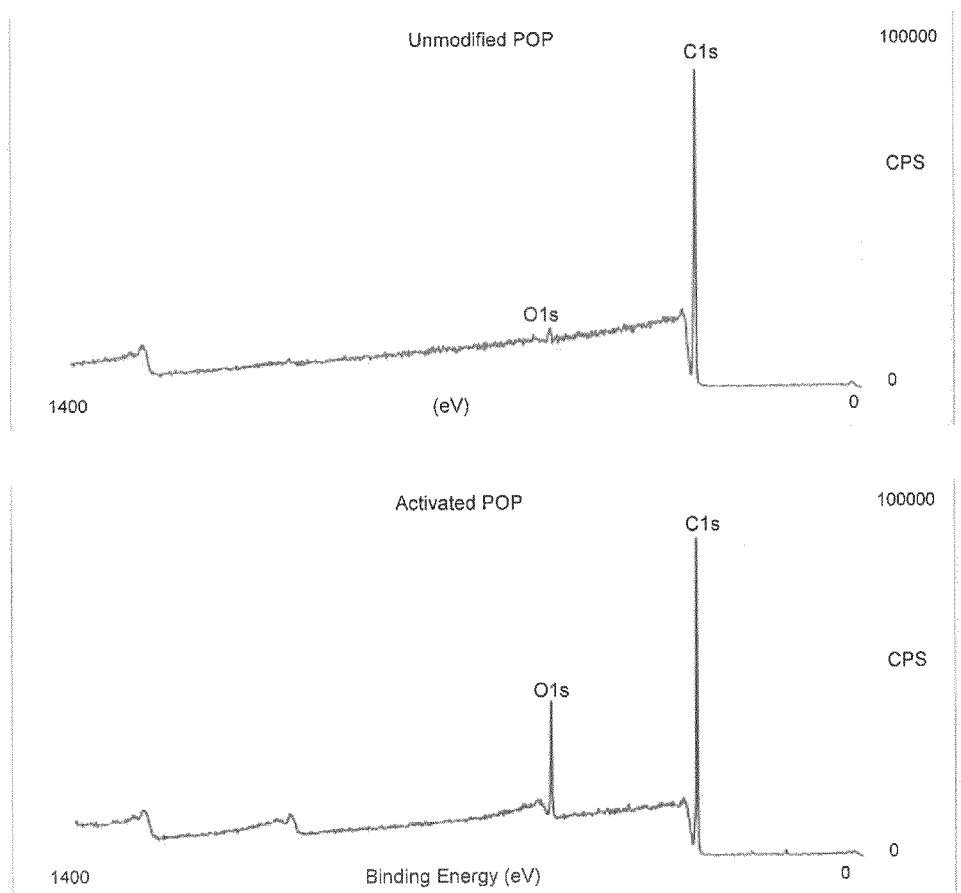
FIG. 12 shows XPS surveys for unmodified versus plasma-activated POP surfaces.

FIG. 12 illustrates binding energy of an unmodified versus plasma-activated surface using XPS analysis.

TABLE 9

POP Surface Properties

| Peak | Unmodified (At. %) | Plasma activation (At. %) | MEG-TFA (At. %) | MEG-OH (At. %) |
|---|---|---|---|---|
| $C_{1s}$ | 96.64 | 86.37 | 66.75 | 84.38 |
| $O_{1s}$ | 2.27 | 12.61 | 19.67 | 11.55 |
| $F_{1s}$ | 0.11 | 0.03 | 5.91 | 0.03 |
| $Si_{2p}$ | 0.40 | 0.19 | 3.91 | 3.84 |

Example 3

Modification of Polyethylene terephthalate) Using Short Chain Silane Adlayers for Removal of Blood Fouling A poly(ethylene terephthalate) surface was modified according to the method described in Example 2.

Formation of a layer is confirmed on the surface. Tests on the surface were conducted using three methods, specifically: contact angle goinometry (CAG), attenuated total reflectance (ATR) and X-ray photoelectron spectroscopy (XPS). All methods confirmed the presence of an adlayer.

Using XPS, the following atoms were analyzed: C, O, N, F, and Si. Atoms exclusive to the layer were present in the coated surfaces with MEG-TFA and MEG-OH having peaks for Si atoms while MEG-TFA also exhibited F atoms.

Figure 17:
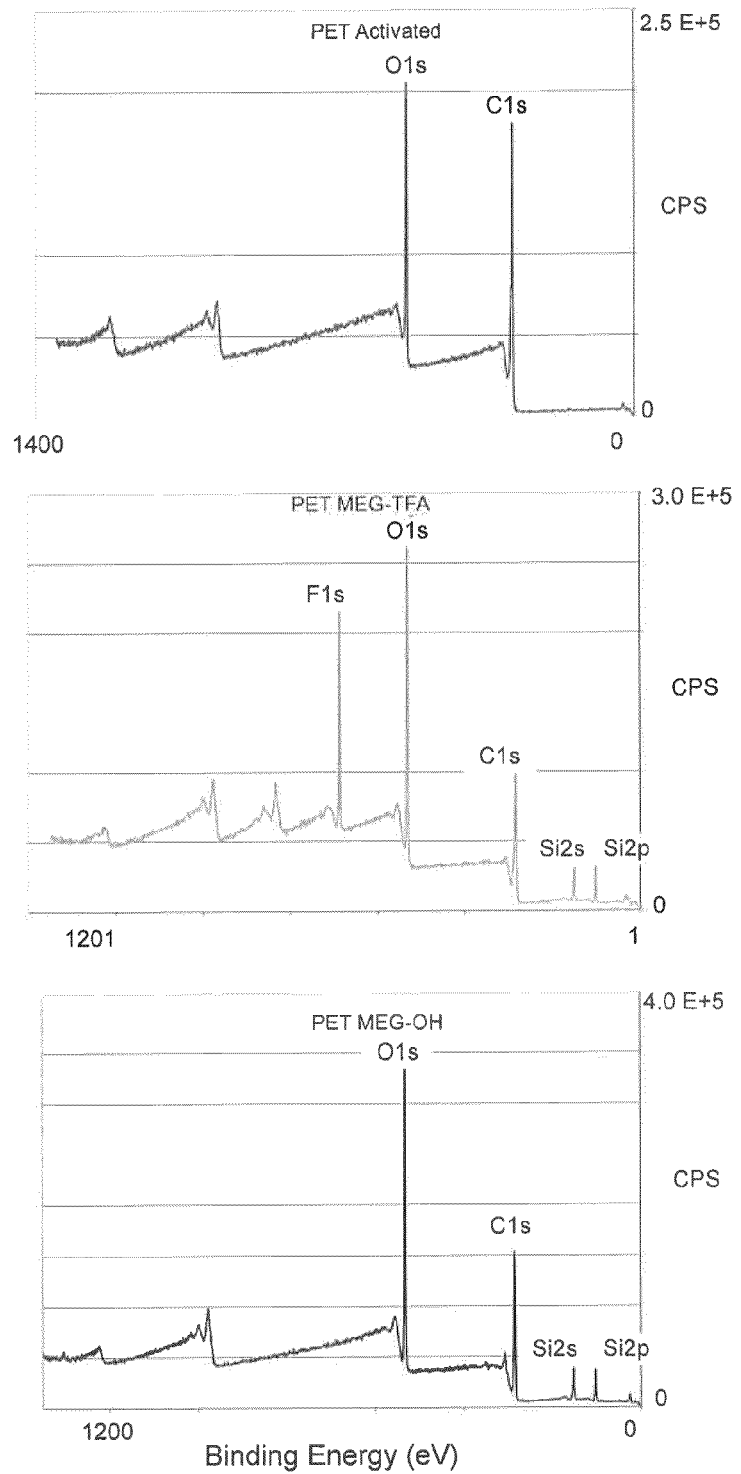
FIG. 17 shows XPS analysis of binding energy of PET for activated, MEG-TFA, and MEG-OH surfaces in Example 3.

FIG. 17 shows XPS analysis of PET for activated (bare), MEG-TFA-, and MEG-OH-coated surfaces.

Using CAG, the calculations of surface energy increase with activation and formation of MEG-OH layer, and decrease with the formation of MEG-TFA layer. Surface energy is linked to the polarity of the surface with activated and MEG-OH surfaces being inherently polar compared to MEG-TFA, which exhibits a non-polar character. Surface energy values were as follows for PET: Unmodified: 30.5 mJ/m$^2$, activated: 48.0 mJ/m$^2$, MEG-TFA: 28.9 mJ/m$^2$, and MEG-OH: 47.0 mJ/m$^2$.

XPS relative elemental percentages are shown in Table 10.

TABLE 10

Elemental Percentages for PET

| Peak | Plasma activation (At. %) | MEG-TFA (At. %) | MEG-OH (At. %) |
|---|---|---|---|
| C1s | 71.45 | 50.49 | 50.67 |
| O1s | 27.69 | 33.87 | 37.67 |
| N1s | 0.30 | 0.12 | 0.35 |

TABLE 10-continued

Elemental Percentages for PET

| Peak | Plasma activation (At. %) | MEG-TFA (At. %) | MEG-OH (At. %) |
|---|---|---|---|
| F1s | 0.00 | 5.43 | 0.03 |
| Si2p | 0.56 | 10.09 | 11.28 |

In ATR-IR, the formation of different types of bonds is seen at different areas: 754, 660-678, 1260 and 1475 cm$^{-1}$, representing different bonds that are exclusive to the coating.

Example 4

Modification of Polycarbonate Using Short Chain Silane Adlayers for Removal of Blood Fouling A polycarbonate surface was modified according to the method described in Example 2.

Formation of a layer is confirmed on the surface. Tests on the surface were conducted using three methods, specifically: contact angle goniometry (CAG), attenuated total reflectance (ATR) and X-ray photoelectron spectroscopy (XPS). All methods confirmed the presence of an adlayer.

Using XPS, the following atoms were analyzed: C, O, N, F, and Si. Atoms prominent to the layer were present in the coated surfaces with MEG-TFA and MEG-OH having peaks for Si atoms while MEG-TFA also exhibited F atoms.

Figure 18:
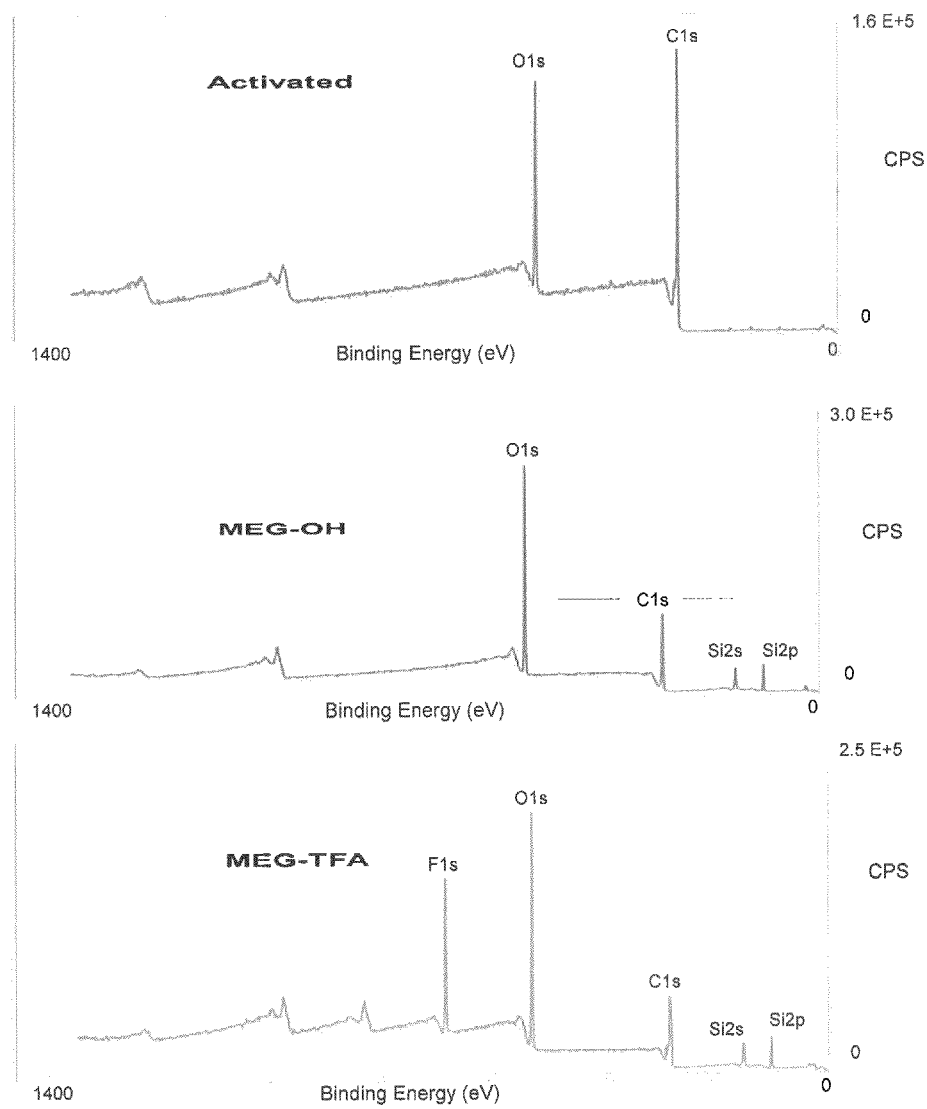
FIG. 18 shows XPS analysis of binding energy of POC for activated, MEG-TFA, and MEG-OH surfaces in Example 4.

FIG. 18 shows XPS analysis of PC for activated (bare), MEG-TFA-, and MEG-OH-coated surfaces.

Using CAG, the calculations of surface energy increase with activation and formation of MEG-OH layer, and decrease with the formation of MEG-TFA layer. Surface energy is linked to the polarity of the surface with activated and MEG-OH surfaces being inherently polar compared to MEG-TFA, which exhibits a non-polar character. Surface energy values were as follows for PC: Unmodified: 25.1 mJ/m$^2$, activated: 47.3 mJ/m$^2$, MEG-TFA: 28.9 mJ/m$^2$, and MEG-OH: 39.8 mJ/m$^2$.

XPS relative elemental percentages are shown in Table 11.

TABLE 11

Elemental Percentages for PC

| Peak | Plasma activation (At. %) | MEG-TFA (At. %) | MEG-OH (At. %) |
|---|---|---|---|
| C1s | 75.61 | 44.72 | 47.44 |
| O1s | 22.62 | 36.74 | 38.89 |
| N1s | 0.84 | 0.04 | 0.13 |
| F1s | 0.01 | 5.92 | 0.1 |
| Si2p | 0.92 | 12.57 | 13.43 |

In ATR-IR, the formation of different types of bonds is seen at different areas: 1020-1080, 1100, 1348, and 1768, 3200-3600 cm$^{-1}$, representing different bonds that are exclusive to the coating.

Example 5

Modification of Polypropylene Using Short Chain Silane Adlayers for Removal of Blood Fouling A polypropylene surface was modified according to the method described in Example 2.

Formation of a layer is confirmed on the surface. Tests on the surface were conducted using three methods, specifically: contact angle goniometry (CAG), attenuated total reflectance (ATR) and X-ray photoelectron spectroscopy (XPS). All methods confirmed the presence of an adlayer.

Using XPS, the following atoms were analyzed: C, O, N, F, and Si. Atoms prominent to the layer were present in the coated surfaces with MEG-TFA and MEG-OH having peaks for Si atoms while MEG-TFA also exhibited F atoms.

Figure 19:
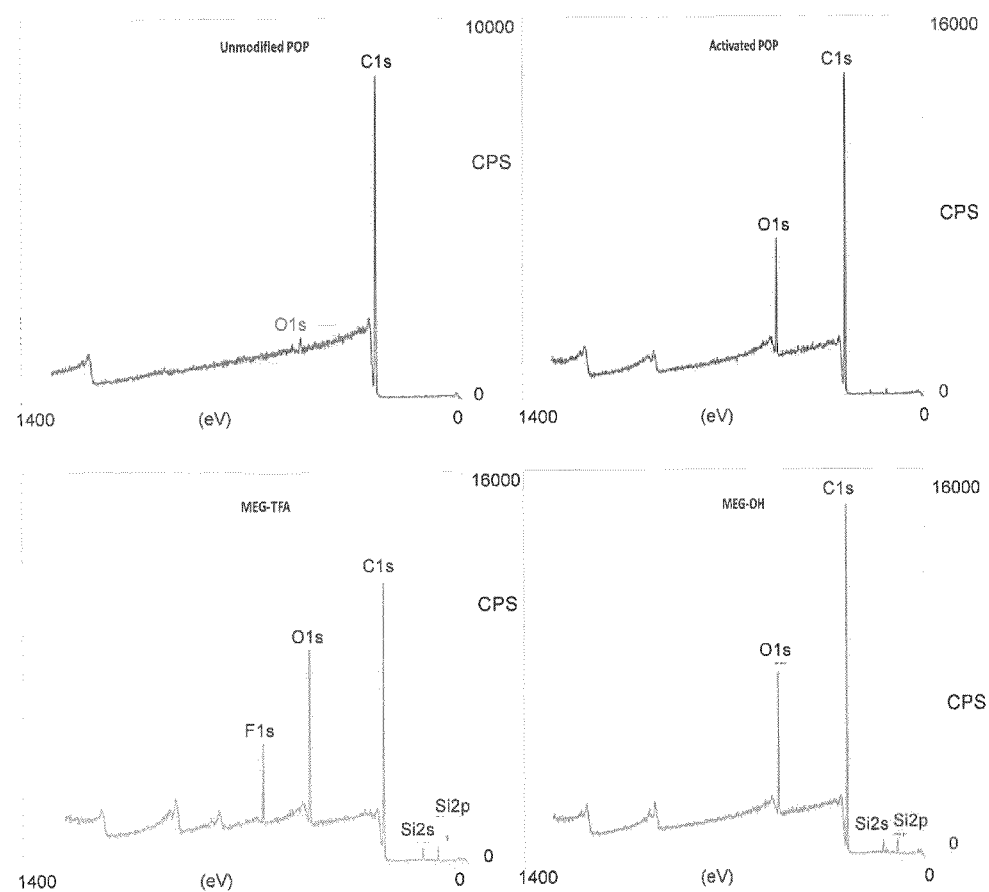
FIG. 19 shows XPS analysis of binding energy of POP for unmodified, activated, MEG-TFA, and MEG-OH surfaces in Example 5.

FIG. 19 shows XPS analysis of POP for unmodified (bare), activated (bare), MEG-TFA-, and MEG-OH-coated surfaces.

Using CAG, the calculations of surface energy increase with activation and formation of MEG-OH layer, and decrease with the formation of MEG-TFA layer. Surface energy is linked to the polarity of the surface with activated and MEG-OH surfaces being inherently polar compared to MEG-TFA, which exhibits a non-polar character. Surface energy values were as follows for POP: Unmodified: 27.9 mJ/m$^2$, activated: 44.1 mJ/m$^2$, MEG-TFA: 27.8 mJ/m$^2$, and MEG-OH: 39.8 mJ/m$^2$.

XPS relative elemental percentages are shown in Table 12.

TABLE 12

Elemental Percentages for POP

| Peak | Unmodified (At. %) | Plasma activation (At. %) | MEG-TFA (At. %) | MEG-OH (At. %) |
|---|---|---|---|---|
| C1s | 96.64 | 86.37 | 66.75 | 84.38 |
| O1s | 2.27 | 12.61 | 19.67 | 11.55 |
| N1s | 0.49 | 0.80 | 0 | 0.03 |
| F1s | 0.11 | 0.03 | 5.91 | 0.20 |
| Si2p | 0.40 | 0.19 | 3.91 | 3.84 |

In ATR-IR, the formation of different types of bonds is seen at different areas: 770, 1795, 3250-3500 cm$^{-1}$, representing different bonds that are exclusive to the coating. Peaks at 770 cm$^{-1}$ represent the C—Si bonding, 1795 cm$^{-1}$ represents C═O bonding and 3200-3500 cm$^{-1}$ represents the likely formation of a water network trapped within the monolayer.

Example 6

Modification of Polyvinyl Chloride Using Short Chain Silane Adlayers for Removal of Blood Fouling A polyvinyl chloride surface was modified according to the method described in Example 2.

Formation of a layer is confirmed on the surface. Tests on the surface were conducted using three methods, specifically: contact angle goniometry (CAG), attenuated total reflectance (ATR) and X-ray photoelectron spectroscopy (XPS). All methods confirmed the presence of an adlayer.

Using XPS, the following atoms were analyzed: C, O, N, F, Si and Cl. Atoms prominent to the layer were present in the coated surfaces with MEG-TFA and MEG-OH having peaks for Si atoms while MEG-TFA also exhibited F atoms.

Figure 20:
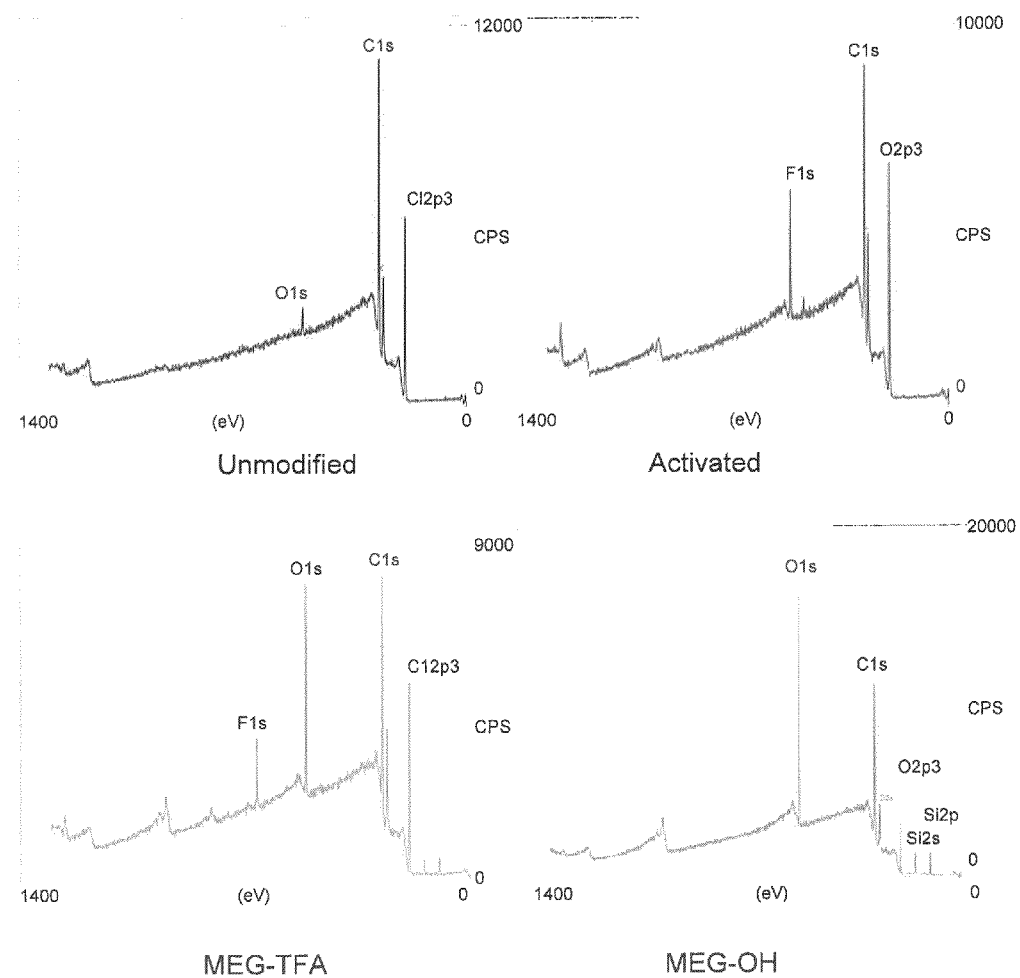
FIG. 20 shows XPS analysis of binding energy of PVC for unmodified, activated, MEG-TFA, and MEG-OH surfaces in Example 6.

FIG. 20 shows XPS analysis of PVC for unmodified (bare), activated (bare), MEG-TFA-, and MEG-OH-coated surfaces.

Using CAG, the calculations of surface energy increase with activation and formation of MEG-OH layer, and decrease with the formation of MEG-TFA layer. Surface energy is linked to the polarity of the surface with activated and MEG-OH surfaces being inherently polar compared to MEG-TFA, which exhibits a non-polar character. Surface energy values were as follows for PVC: Unmodified: 31.5 mJ/m$^2$, activated: 40.4 mJ/m$^2$, MEG-TFA: 33.0 mJ/m$^2$, and MEG-OH: 39.9 mJ/m$^2$.

XPS relative elemental percentages are shown in Table 13.

TABLE 13

Elemental Percentages for PVC

| Peak | Unmodified (At. %) | Plasma activation (At. %) | MEG-TFA (At. %) | MEG-OH (At. %) |
|---|---|---|---|---|
| C1s | 77.18 | 64.09 | 57.25 | 53.92 |
| O1s | 2.95 | 11.81 | 17.04 | 24.00 |
| N1s | 0.56 | 1.49 | 0.69 | 0.52 |
| F1s | 0.28 | 0.25 | 1.84 | 0.21 |
| Si2p | 0.15 | 0.51 | 5.10 | 8.10 |
| Cl2p | 18.88 | 21.85 | 18.08 | 13.25 |

In ATR-IR, the formation of different types of bonds is seen at different areas: 634, 1674-1789, and 2339-2362 cm$^{-1}$, representing different bonds that are exclusive to the coating.

Example 7

Modification of Polyurethane Using Short Chain Silane Adlayers for Removal of Blood Fouling A polyurethane surface is modified according to the method described in Example 2.

Results show that the contact angle with water decreased from ~100° to ~15° upon activation. When the MEG-TFA layer is formed, the contact angle of water increases to 90°, which is consistent with a decrease in polarity of the surface. Formation of MEG-OH reduces the angle to 55°. Data confirms that the layer is deposited on polyurethane, because MEG-TFA films display non polar TFA groups resulting in a higher contact angle when compared to the polar MEG-OH coatings. Analysis with ATR-IR shows main peaks at 1793 and 3400-3550 cm$^{-1}$, representing C=O and water hydrogen bonding inside the layer. Other important peaks are seen at 1263, 1731, 1793, 2341-2363 and 3400-3550 cm$^{-1}$.

Example 8

Modification of Poly(methyl methacrylate) Using Short Chain Silane Adlayers for Removal of Blood Fouling A poly(methyl methacrylate) surface is modified according to the method described in Example 2.

Formation of a layer is confirmed on the surface. Tests on the surface were conducted using three methods, specifically: contact angle goniometry (CAG), attenuated total reflectance (ATR) and X-ray photoelectron spectroscopy (XPS). All methods confirmed the presence of an adlayer.

Using XPS, the following atoms were analyzed: C, O, N, F, and Si. Atoms prominent to the layer were present in the coated surfaces with MEG-TFA and MEG-OH having peaks for Si atoms while MEG-TFA also exhibited F atoms.

Figure 21:
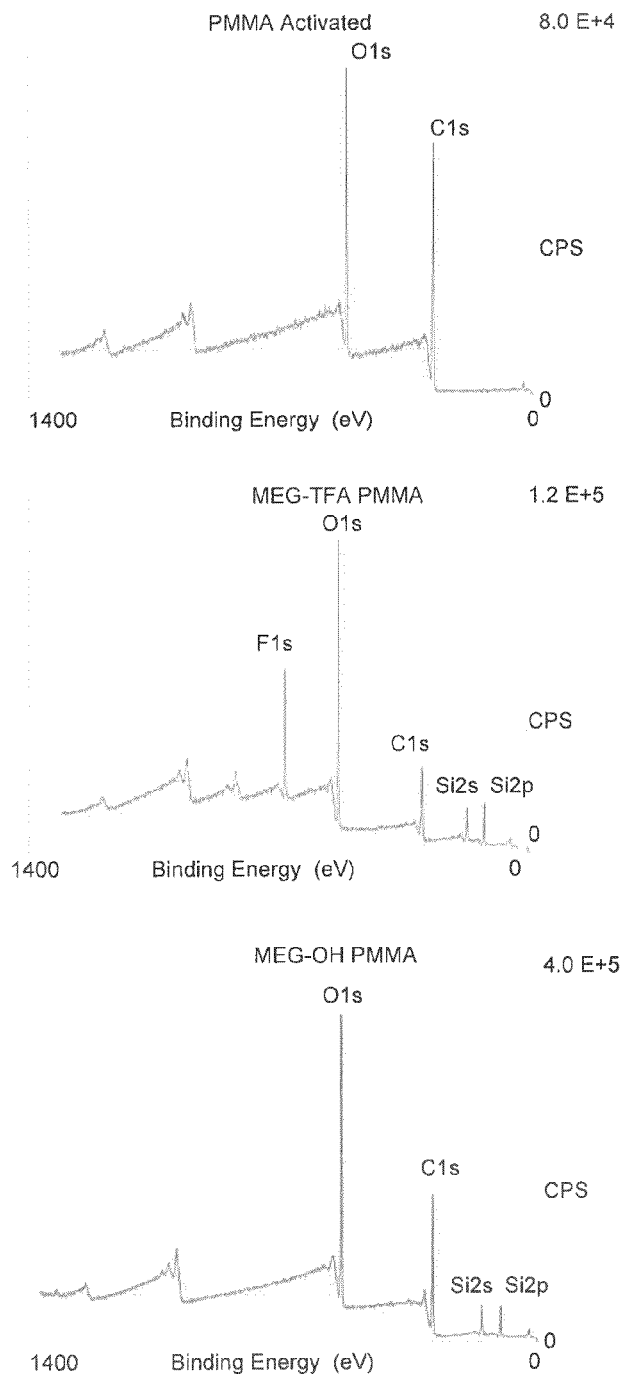
FIG. 21 shows XPS analysis of binding energy of poly (methyl methacrylate) for activated, MEG-TFA, and MEG-OH surfaces in Example 8.

FIG. 21 shows XPS analysis of PMMA for activated (bare), MEG-TFA-, and MEG-OH-coated surfaces.

Using CAG, the calculations of surface energy increase with activation and formation of MEG-OH layer, and decrease with the formation of MEG-TFA layer. Surface energy is linked to the polarity of the surface with activated and MEG-OH surfaces being inherently polar compared to MEG-TFA, which exhibits a non-polar character. Surface energy values were as follows for PMMA: Unmodified: 34.3 mJ/m$^2$, activated: 45.1 mJ/m$^2$, MEG-TFA: 26.6 mJ/m$^2$, and MEG-OH: 48.0 mJ/m$^2$.

XPS relative elemental percentages are shown in Table 14.

TABLE 14

Elemental Percentages for PMMA

| Peak | Plasma activation (At. %) | MEG-TFA (At. %) | MEG-OH (At. %) |
|---|---|---|---|
| C1s | 44.42 | 18.07 | 29.10 |
| O1s | 54.27 | 51.48 | 64.65 |
| F1s | 1.06 | 25.37 | 0 |
| Si2p | 0.25 | 5.07 | 6.25 |

In ATR-IR, the formation of different types of bonds is seen at different areas: 800-900, 900-1000, 1100-1170, and 1280-1340 cm$^{-1}$, representing different bonds that are exclusive to the coating.

Figure 22:
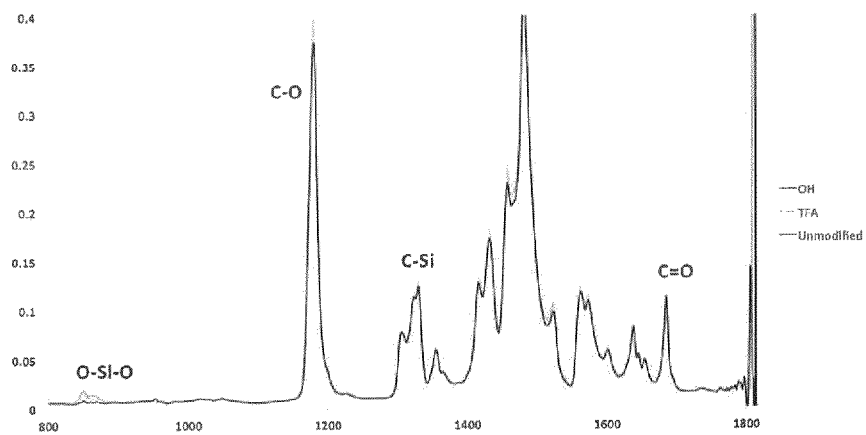
FIG. 22 shows an infrared spectrum showing O—Si—O, C—O, C—Si, and C=O bands for modified and unmodified poly(methyl methacrylate) surfaces.

FIG. 22 shows a spectrum depicting O—Si—O, C—O, C—Si, and C=O bonds for a poly(methyl methacrylate) surface either functionalized with MEG-OH or MEG-TFA versus an unmodified surface. Three important peaks are depicted in more detail in FIG. 23a, FIG. 23b, and FIG. 23c.

Figure 23A:
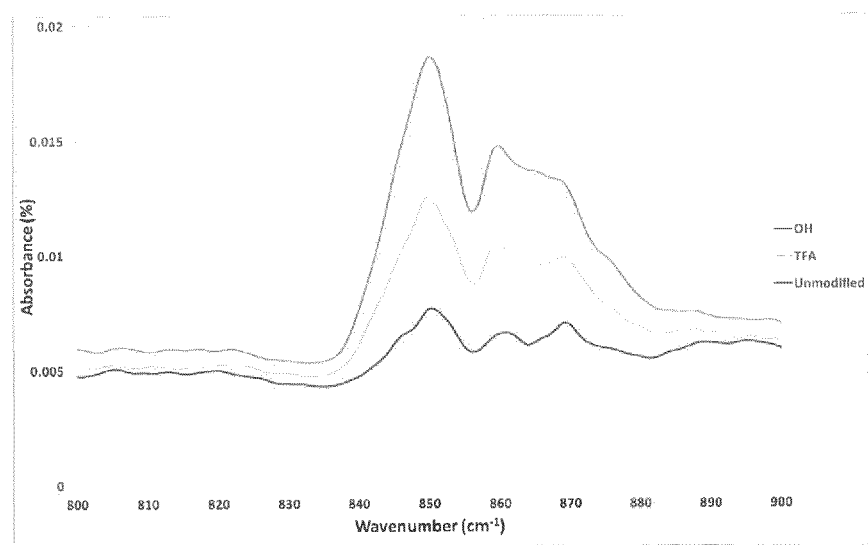
FIG. 23a illustrates a schematic representation of three different poly(methyl methacrylate) surfaces: unmodified, and modified with MEG-TFA and MEG-OH and shows O—Si—O IR bands for MEG-OH, MEG-TFA, and unmodified poly(methyl methacrylate) surfaces.

FIG. 23a illustrates a schematic representation of three different poly(methyl methacrylate) surfaces: unmodified, and modified with MEG-TFA and MEG-OH, and shows O—Si—O IR bands for MEG-OH, MEG-TFA, and unmodified poly(methyl methacrylate) surfaces.

Figure 23B:
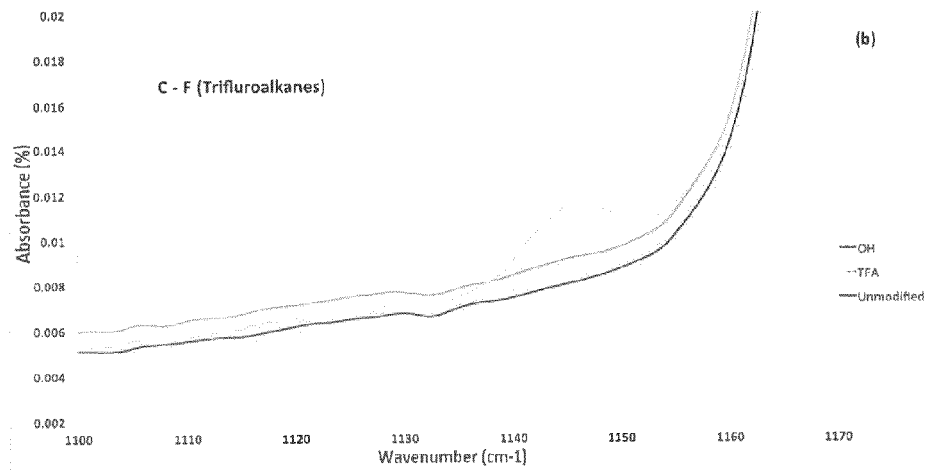
FIG. 23b shows the C—F (trifluoroacetyl) band (or lack) for MEG-OH, MEG-TFA, and unmodified poly(methyl methacrylate) surfaces.

FIG. 23b shows the C—F (trifluoroacetyl) band (or lack) for MEG-OH, MEG-TFA, and unmodified poly(methyl methacrylate) surfaces.

Figure 23C:
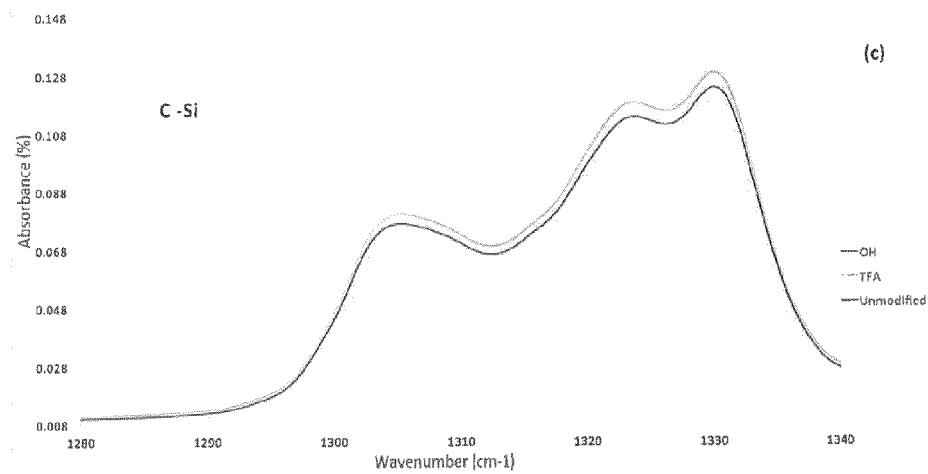
FIG. 23c shows the C—Si band for MEG-OH, MEG-TFA, and unmodified poly(methyl methacrylate) surfaces.

FIG. 23c shows the C—Si band for MEG-OH, MEG-TFA, and unmodified poly(methyl methacrylate) surfaces.

These data illustrate that poly(methyl methacrylate) was effectively functionalized with a self-assembling monolayer in accordance with the method described herein.

In the preceding description, for purposes of explanation, numerous details are set forth in order to provide a thorough understanding of the. However, it will be apparent to one skilled in the art that these specific details are not required in order to practice the invention.

The above-described embodiments are intended to be examples only. Alterations, modifications and variations can be effected to the particular embodiments by those of skill in the art without departing from the scope of the invention, which is defined solely by the claims appended hereto.

All references cited herein are incorporated by reference.

REFERENCES 1. a) Eggins, B. R. In *Chemical Sensors and Biosensors*; John Wiley & Sons Ltd.: Chichester, UK, 2002. b) Collings A. F.; Caruso, F. *Rep. Prog. Phys.* 1997, 60, 1397.
2. Sadik, O. A.; Ngundi, M. M.; Yan, F. *Biotechnol. Bioproc. Eng.* 2000, 5, 407.
3. Del Carlo, M.; Nistor, M.; Campagnone, D.; Mattiasson, B.; Csoregi, E. In *Food Biotechnology* (2nd Edition); Shetty, K.; Paliyath, G.; Pometto, A.; Levin, R. E. Eds.; Taylor & Francis Group: Boca Raton, Fla., USA, 2006, p 1567.
4. Yu, D.; Blankert, B.; Vire, J.-C.; Kauffmann, J.-M. *Anal. Lett.* 2005, 38, 1687.
5. Gooding, J. J. *Anal. Chim. Acta* 2006, 559, 137.
6. Yang, V. C.; Ngo, T. T. In *Biosensors and Their Applications*; Kluwer Academic/Plenum Publishers: New York, USA, 2000.
7. a) Rusmini, F.; Zhong, Z. Y.; Feijen, J. *Biomacromolecules* 2007, 8, 1775. b) Kim, D. C.; Kang, D. J. *Sensors* 2008, 8, 6605.

8. a) Vericat, C.; Vela, M. E.; Benitez, G. A.; Martin Gago, J. A.; Torrelles, X.; Salvarezza, R. C. *J. Phys.: Condens. Matter* 2006, 18, R867. b) Shenhar, R.; Norsten, T. B.; Rotello, V. M. In *Introduction to Nanoscale Science and Technology*, Di Ventra, M.; Evoy, S.; Heflin, J. R. Eds.: Springer: New York, USA, 2004, p 41. c) Ulman, A. *Chem. Rev.* 1996, 96, 1533.
9. a) Camarero, J. A. *Biophys. Rev. Lett.* 2006, 1, 1. b) Lee, Y. W.; Reed-Mundell, J.; Zull, J. E.; Sukenik, C. N. *Langmuir* 1993, 9, 3009.
10. Azioune, A.; Pireaux, J.-J.; Houssiau, L. *Appl. Surf. Sci.* 2004, 231-2, 402.
11. a) Chrisey, L. A.; Lee, G. U.; O'Ferrall, C. E. *Nucleic Acids Res.* 1996, 24, 3031. b) Saoud, M.; Blaszykowski, C.; Ballantyne, S. M.; Thompson, M. *Analyst* 2009, 134, 835.
12. a) Wink, T.; van Zuilen, S. J.; Bult, A.; van Bennekom, W. P. *Analyst* 1997, 122, 43R. b) Chaki, N. K.; Vijayamohanan, K. *Biosens. Bioelectron.* 2002, 17, 1. c) Luderer, F.; Walschus, U. *Top. Curr. Chem.* 2005, 260, 37. d) Ferretti, S.; Paynter, S.; Russell, D. A.; Sapsford, K. E.; Richardson, D. J. *Trends Anal. Chem.* 2000, 19, 530. e) Liedberg, B.; Cooper, J. M. In *Immobilized Biomolecules in Analysis: A practical Approach*; Cass, T.; Ligler, F. S. Eds.: Oxford University Press, Oxford, UK, 1998, p 55.
13. a) Guilbault, G. G.; Jordan, J. M.; Scheide, E. *CRC Crit. Rev. Anal. Chem.* 1988, 19, 1. b) Deakin, M. R.; Buttry, D. A. *Anal. Chem.* 1989, 61, 1147A.
14. a) Sheikh, S.; Blaszykowski, C.; Thompson, M. *Anal. Lett.* 2008, 41, 2525. b) Gronewold, T. M. A. *Anal. Chim. Acta* 2007, 603, 119.
15. Selected reviews: a) Rickert, J.; Gopel, W.; Hayward, G. L.; Čavić, B. A.; Thompson, M. In *Sensors Update (Volume 5)*; Baltes, H.; Gopel, W.; Hesse, J. Eds.; Wiley-VCH: Weinheim, Germany, 1999, p 105. b) Čavić, B. A.; Hayward, G. L.; Thompson, M. *Analyst* 1999, 124, 1405. c) Cooper, M. A.; Singleton, V. T. *J. Mol. Recognit.* 2007, 20, 154. d) Länge, K.; Rapp, B. E.; Rapp, M. *Anal. Bioanal. Chem.* 2008, 391, 1509.
16. a) Thompson, M.; Ballantyne, S. M.; Cheran, L.-E.; Stevenson, A. C.; Lowe, C. R. *Analyst* 2003, 128, 1048. b) Thompson, M.; Ballantyne, S. M. *Electromagnetic piezoelectric acoustic sensor* 2007, U.S. Pat. No. 7,207,222.
17. Ballantyne, S. M.; Thompson, M. *Analyst* 2004, 129, 219.
18. a) McGovern, M. E.; Thompson, M. *Anal. Commun.* 1998, 35, 391. b) McGovern, M. E.; Thompson, M. *Can. J. Chem.* 1999, 77, 1678.
19. Savage, M. D.; Mattson, G.; Desai, S.; Nielander, G. W.; Morgensen, S.; Conklin, E. J. In *Avidin-Biotin Chemistry: A Handbook*; Pierce Chemical Company: Rockford, Ill., USA, 1992.
20. Wasserman, S. R.; Tao, Y.-T.; Whitesides, G. M. *Langmuir* 1989, 5, 1074.
21. Fryxell, G. E.; Rieke, P. C.; Wood, L. L.; Engelhard, M. H.; Williford, R. E.; Graff, G. L.; Campbell, A. A.; Wiacek, R. J.; Lee, L.; Halverson, A. *Langmuir* 1996, 12, 5064.
22. Lee, J. W.; Sim, S. J.; Cho, S. M.; Lee, J. *Biosens. Bioelectron.* 2005, 20, 1422.
23. a) Anderson, A. S.; Dattelbaum, A. M.; Mukundan, H.; Price, D. N.; Grace, W. K.; Swanson, B. I. In *Proceedings of SPIE, Frontiers in Pathogen Detection: From Nanosensors to Systems (Films and Substrates)*; Fauchet, M. Ed.; 2009, 7167, 7167Q1. See also: b) Zheng, J.; Li, L.; Tsao, H.-K.; Sheng, Y.-J.; Chen, S.; Jiang, S.; *Biophys. J.* 2005, 89, 158.
24. a) Ostuni, E.; Chapman, R. G.; Holmlin, R. E.; Takayama, S.; Whitesides, G. M. *Langmuir* 2001, 17, 5605. b) Ngadi, N.; Abrahamson, J.; Fee, C.; Morison, K. *WASET: Engineering and Technology (proceedings)* 2009, 49, 144. c) Snellings, G. M. B. F.; Vansteenkiste, S. O.; Corneillie, S. I.; Davies, M. C.; Schacht, E. H. *Adv. Mater.* 2000, 12, 1959. d) Ostuni, E.; Chapman, R. G.; Liang, M. N.; Meluleni, G.; Pier, G.; Ingber, D. E.; Whitesides, G. M. *Langmuir* 2001, 17, 6336. e) Xia, N.; Hu, Y.; Grainger, D. W.; Castner, D. G. *Langmuir* 2002, 18, 3255. f) Jeon, S. I.; Lee, J. H.; Andrade, J. D.; De Gennes, P.-G. *J. Colloid Interface Sci.* 1991, 142, 149.
25. a) Parsons, T. F.; Buckman, J. D.; Pearson, D. E.; Field, L. *J. Org. Chem.* 1965, 30, 1923. b) Kice, J. L.; Rogers, T. E. *J. Am. Chem. Soc.* 1974, 96, 8015.
26. a) Delgado, M.; Martin, J. D. *J. Org. Chem.* 1999, 64, 4798. b) Doyle, M. P.; Hu, W. *J. Org. Chem.* 2000, 65, 8839.
27. Corona, C.; Bryant, B. K.; Arterburn, J. B. *Org. Lett.* 2006, 8, 1883.
28. DeLaLuz, P. J.; Golinski, M.; Watt, D. S.; Vanaman, T. C. *Bioconjugate Chem.* 1995, 6, 558.
29. Galonić, D.; Ide, N. D.; van der Donk, W. A.; Gin, D. Y. *J. Am. Chem. Soc.* 2005, 127, 7359.
30. Sarkar, S.; Sales, K. M.; Hamilton, G.; Seifalian, A. M. *J. Biomed. Mater. Res. B* 2007, 82(1), 100.
31. De Mel, A.; Cousins, B. G.; Seifalian, A. M. *Int. J. Biomater.* 2012, 2012, 707863.
32. Sheikh, S.; Yang, D. Y.; Blaszykowski, C.; Thompson, M. *Chem. Commun.* 2012, 48(9), 1305.
33. Rjeb, A.; Letarte, S.; Tajounte, L.; El Idrissi, M. C.; Adnot, A.; Roy, D.; Clare, Y.; Kalwstian, J. *J. Electron. Spectrosc.* 2000, 107(3), 221.
34. Sorarù, G. D.; D'Andrea, G.; Glisenti, A. *Mater. Lett.* 1996, 27(1-2), 1.
35. Hijikata, Y.; Yaguchi, H.; Yoshikawa, M.; Yoshida, S. *Appl. Surf. Sci.* 2001, 184(1-4), 161.
36. Jing, S.; Lee, H.; Choi, C. K. *J. Korean Phys. Soc.* 2002, 41(5), 769.
37. Jing, S.; Lee, H.; Choi, C. K. *J. Korean Phys. Soc.* 2002, 41(5), 769.
38. De, G.; Kundu, D.; Karmakar, B.; Ganguli, D. *J. Non-Cryst. Solids.* 1993, 155(3), 253.
39. Ou, D. L.; Seddon, A. B. *J. Non-Cryst. Solids.* 1997, 210(2-3), 187.
40. Silberzan, P.; Léger, L.; Ausserré, D.; Benattar, J. J. *Langmuir* 1991, 7(8), 1647.
41. Van Oss, C. J.; Chaudhury, M. K.; Good, R. J. *Chem Rev.* 1988, 88(6), 927.

What is claimed is:

1. A surface-modified polymer comprising a polymeric material and a self-assembling monolayer covalently bound on the surface of the polymeric material, wherein the monolayer comprises 2-(3-trichlorosilyl-propyloxy)-ethyl-trifluoroacetate (7-OEG or MEG-TFA); 2,2,2-trifluoroethyl-13-trichlorosilyl-tridecanoate (TTTA); OEGylated TTTA (OEG-TTTA); S-(2-(2-(2-(3-trichlorosilyl-propyloxy)-ethoxy)-ethoxy)-ethyl)-benzenethiosulfonate (OEG-TUBTS); or a combination thereof.

2. The polymer of claim 1, wherein the monolayer additionally comprises octyltrichlorosilane (OTS).

3. The polymer of claim 1, wherein the monolayer comprises monoethylene glycolated trifluoroacetate (MEG-TFA).

4. The polymer of claim 1, wherein the monolayer comprises a mixture of 2,2,2-trifluoroethyl-13-trichlorosilyl-tridecanoate (TTTA) and OTS.

5. The polymer of claim 1, wherein the monolayer comprises a mixture of OEGylated 2,2,2-trifluoroethyl-13- trichlorosilyl-tridecanoate (OEG-TTTA) and 2-(3-trichlorosilyl-propyloxy)-ethyl-trifluoroacetate (7-OEG).

6. The polymer of claim 1, wherein the monolayer comprises a mixture of S-(2-(2-(2-(3-trichlorosilyl-propyloxy)-ethoxy)-ethoxy)-ethyl)-benzenethiosulfonate (OEG-TUBTS) and 2-(3-trichlorosilyl-propyloxy)-ethyl-trifluoroacetate (7-OEG).

7. The polymer of claim 1, wherein the polymeric material comprises available hydroxyl groups.

8. The polymer of claim 1, wherein the polymeric material comprises polycarbonate, poly(ethylene terephthalate), polypropylene, polyvinyl chloride, polyurethane, poly(methyl methacrylate), nylon, polyethylene, or combinations thereof.

9. The polymer of claim 7, wherein the polymeric material comprises polycarbonate.

10. A method of forming a surface-modified polymer having a self-assembling monolayer thereon, the method comprising the activation of the surface of a polymeric material to generate hydroxyl groups thereon and silanizing the activated surface with a monolayer comprised of monoethylene glycolated-OH (MEG-OH); 2-(3-trichlorosilyl-propyloxy)-ethyl-trifluoroacetate (7-OEG or MEG-TFA); 2,2,2-trifluoroethyl-13-trichlorosilyl-tridecanoate (TTTA); OEGylated TTTA (OEG-TTTA); S-(2-(2-(2-(3-trichlorosilyl-propyloxy)-ethoxy)-ethoxy)-ethyl)-benzenethiosulfonate (OEG-TUBTS); or a combination thereof.

11. The method of claim 10, wherein activating the surface comprises exposure to plasma.

12. The method of claim 10, wherein the monolayer additionally comprises octyltrichlorosilane (OTS).

13. The method of claim 10, wherein the monolayer comprises MEG-TFA.

14. The method of claim 10, wherein the monolayer comprises MEG-OH.

15. The method of claim 10, wherein the monolayer comprises a mixture of TTTA and OTS.

16. The method of claim 10, wherein the monolayer comprises a mixture of OEG-TTTA and 7-OEG.

17. The method of claim 10, wherein the monolayer comprises a mixture of OEG-TUBTS and 7-OEG.

18. The method of claim 10, wherein the polymeric material comprises polycarbonate, poly(ethylene terephthalate), polypropylene, polyvinyl chloride, polyurethane, poly(methyl methacrylate), nylon, polyethylene, or combinations thereof.

19. A method of preventing or reducing fouling of a polymer upon contact with a biological fluid, comprising modifying the surface of the polymer with a covalently bound self-assembling monolayer, wherein the monolayer comprises monoethylene glycolated-OH (MEG-OH); 2-(3-trichlorosilyl-propyloxy)-ethyl-trifluoroacetate (7-OEG or MEG-TFA); 2,2,2-trifluoroethyl-13-trichlorosilyl-tridecanoate (TTTA); OEGylated TTTA (OEG-TTTA); S-(2-(2-(2-(3-trichlorosilyl-propyloxy)-ethoxy)-ethoxy)-ethyl)-benzenethiosulfonate (OEG-TUBTS); or a combination thereof, and wherein the polymer is formed of a polymeric material having hydroxyl groups thereon, comprising polycarbonate, poly(ethylene terephthalate), polypropylene, polyvinyl chloride, polyurethane, poly(methyl methacrylate), nylon, polyethylene or combinations thereof.

20. The method of claim 19, wherein preventing or reducing fouling comprises preventing or reducing thrombus or clot formation, the biological fluid being blood.

21. The polymer of claim 1, wherein the monolayer additionally comprises monoethylene glycolated-OH (MEG-OH).

\* \* \* \* \*